US007235628B2

(12) United States Patent
Dong

(10) Patent No.: US 7,235,628 B2
(45) Date of Patent: Jun. 26, 2007

(54) ANALOGUES OF GLP-1

(75) Inventor: Zheng Xin Dong, Holliston, MA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 11/145,782

(22) Filed: Jun. 6, 2005

(65) Prior Publication Data

US 2005/0233969 A1 Oct. 20, 2005

Related U.S. Application Data

(63) Continuation of application No. 09/857,636, filed as application No. PCT/EP99/09660 on Dec. 7, 1999, now Pat. No. 6,903,186, and a continuation-in-part of application No. 09/206,601, filed on Dec. 7, 1998, now abandoned.

(60) Provisional application No. 60/111,255, filed on Dec. 7, 1998.

(51) Int. Cl.
*C07K 14/435* (2006.01)
*C07K 14/605* (2006.01)
(52) U.S. Cl. .................. 530/324; 514/12; 530/308
(58) Field of Classification Search .................. 514/12; 530/308, 324
See application file for complete search history.

(56) References Cited

U.S. PATENT DOCUMENTS

| 5,512,549 | A | 4/1996 | Chen et al. |
|---|---|---|---|
| 5,545,618 | A | 8/1996 | Buckley et al. |
| 5,705,483 | A | 1/1998 | Galloway et al. |
| 6,214,547 | B1 | 4/2001 | Kjeldsen et al. |
| 6,410,513 | B1 | 6/2002 | Galloway et al. |
| 6,458,924 | B2 | 10/2002 | Knudsen et al. |
| 6,620,910 | B1 | 9/2003 | Calas et al. |
| 6,720,407 | B1 | 4/2004 | Hughes et al. |
| 6,903,186 | B1 | 6/2005 | Dong et al. |

FOREIGN PATENT DOCUMENTS

| CA | 2 352 573 | 6/2000 |
|---|---|---|
| EP | 0 658 568 A1 | 6/1995 |
| EP | 0 699 686 A2 | 3/1996 |
| EP | 0 699 686 A3 | 3/1996 |
| EP | 0 708 179 A2 | 4/1996 |
| EP | 0 708 179 A3 | 4/1996 |
| EP | 0 733 644 A1 | 9/1996 |
| EP | 0 869 135 A1 | 10/1998 |
| WO | WO 87/06941 | 11/1987 |
| WO | WO 91/11457 | 8/1991 |
| WO | WO 97/29180 | 8/1997 |
| WO | WO 98/03547 | 1/1998 |
| WO | WO 98/08871 | 3/1998 |
| WO | WO 98/19698 | 5/1998 |
| WO | 99/43705 | 9/1999 |
| WO | 00/34331 | 6/2000 |
| WO | 01/035988 | 5/2001 |

OTHER PUBLICATIONS

Adelhorst, K. et al., "Structure-activity studies of glucogen-like peptide-1," 1994, J. Biological Chemistry, 269 (9) :6275-6278.
Parker, J.C., e al.; "Structure-function analysis of a series of glucagon-like peptide-1 analogs"; 1998; Peptide Res; pp. 398-409; XP-000788444.
Ritzel, U. et al., "A synthetic glucogen-like peptide-1 analog with improved plasma stability," 1998, J. Endocrinology, 159:93-102.
Thorens, Bernard, et al.; "Glucagon-Like Peptide-I and the Control of Insulin Secretion in the Normal State and in NIDDM"; 1993; Diabetes; vol. 42; pp. 1219-1225.
Ahren, Bo, et al.; "Effects of Glucagon-Like Peptide-1 on Islet Function and Insulin Sensitivity in Noninsulin-Dependent Diabetes Mellitus"; 1997; Journal of Clinical Endocrinology and Metabolism; vol. 82.2; pp. 473478.
Deacon, C.F., et al.; "Dipeptidyl peptidase IV resistant analogues of glucagon-like peptide-1 which have extended metabolic stability and improved biological activity"; 1998; Diabetologia; vol. 41; pp. 271-278.
Deacon, C.F., et al., "Dipeptidyl Peptidase IV Inhibition Potentiates the Insulinotropic Effect of Glucagon-Like Peptide 1 in the Anesthetized Pig"; 1998; Diabetes; vol. 47; pp. 764-769.
Gutniak, Mark, et al.; "Antidiabetogenic Effect of Glucagon-Like Peptide-1 (7-36) Amide in Normal Subjects and Patients with Diabetes Mellitus"; The New England Journal of Medicine; vol. 326; pp. 1316-1322.
Mentlein, R., et al; "Dipeptidyl-peptidase IV hydrolyses gastric inhibitory polypeptide, ducagon-like peptide-1 (7-36) amide, peptide histidine methionine and is responsible for their degradation in human serum"; 1993; Biochem; vol. 214; pp. 829-835.
Nauck, M.A., et al.; "Effects of subcutaneous glucagon-like peptide 1 (GLP-1 [7-36 amide]) in patients with NIDDM"; 1996; Diabetologia; vol. 82:2; pp. 1546-1553.
Rachman, J., et al.; "Near-normalisation of diurnal glucose concentrations by continuous administration of glucagon-like peptide-1 (GLP-1) in subjects with NIDDM"; 1997; Diabetologia; vol. 40; pp. 205-211.
Suzuki, S., et al.; "Comparison of the Effects of Various C-Terminal and N-Terminal Fragment Peptide of Glucagon-Like Peptide-1 on Insulin and Glucagon Release from the Isolated Perfused Rat Pancreas"; 1989; Endocrinology; vol. 125:6; pp. 3109-3114.
Thorens, Bernard, et al.; "Structure and Function of the Glucagon-Like Peptide-1 Receptor"; 1996; Journal: Handbook of Experimental Pharmacology; vol. 123; pp. 255-273.
Todd, J.F., et al.; "Glucagon-like peptide-1 (GLP-1): a trial of treatment in non-insulin-dependent diabetes mellitus"; 1997; European Jouranl of Clinical Investigation; vol. 27; pp. 533-536.
Mojsov, S. "Structural requirements for biological activity of glucagon-like peptide I,"Int. J. Pep. Res., 1992, 40:333-343.
Abstract from Hungarian Patent P9501508, Feb. 1997.

Primary Examiner—David Lukton
(74) Attorney, Agent, or Firm—Fish & Richardson; Alan F. Feeney; Tony K. Uhm

(57) ABSTRACT

The present invention is directed to peptide analogues of glucagon-like peptide-1, the pharmaceutically-acceptable salts thereof, to methods of using such analogues to treat mammals and to pharmaceutical compositions useful thereof comprising said analogues.

1 Claim, No Drawings

ANALOGUES OF GLP-1

CROSS-REFERENCE TO RELATED APPLICATIONS

This application is a continuation of U.S. application Ser. No. 09/857,636, filed Nov. 2, 2001, now U.S. Patent No. 6,903,186 which is a National Phase filed under 35 U.S.C. 371 of International Application No. PCT/EP99/09660, filed Dec. 7, 1999, and a continuation-in-part of U.S. application Ser.No. 09/206,601, filed Dec. 7, 1998, now abandoned, which claims the benefit of U.S. application Ser. No. 60/111,255, filed Dec. 7, 1998, the contents of which are incorporated herein by reference.

BACKGROUND OF THE INVENTION

The present invention is directed to peptide analogues of glucagon-like peptide-1, the pharmaceutically-acceptable salts thereof, to methods of using such analogues to treat mammals and to pharmaceutical compositions useful thereof comprising said analogues.

Glucagon-like peptide-1 (7-36) amide (GLP-1) is synthesized in the intestinal L-cells by tissue-specific post-translational processing of the glucagon precursor preproglucagon (Varndell, J. M., et al., J. Histochem Cytochem, 1985: 33:1080-6) and is released into the circulation in response to a meal. The plasma concentration of GLP-1 rises from a fasting level of approximately 15 pmol/L to a peak postprandial level of 40 pmol/L. It has been demonstrated that, for a given rise in plasma glucose concentration, the increase in plasma insulin is approximately threefold greater when glucose is administered orally compared with intravenously (Kreymann, B., et al., Lancet 1987:2, 1300-4). This alimentary enhancement of insulin release, known as the incretin effect, is primarily humoral and GLP-1 is now thought to be the most potent physiological incretin in humans. In addition to the insulinotropic effect, GLP-1 suppresses glucagon secretion, delays gastric emptying (Wettergren A., et al., Dig Dis Sci 1993:38:665-73) and may enhance peripheral glucose disposal (D'Alessio, D. A. et al., J. Clin Invest 1994: 93:2293-6).

In 1994,the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K., et al., Diabetes Care 1994:17:1039-44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327-32). Unlike sulphonylureas, the insulinotropic action of GLP-1 is dependent on plasma glucose concentration (Holz, G. G. 4$^{th}$, et al., Nature 1993: 361:362-5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701-711, 1992; Holst, J. J., et al., *Potential of GLP-1 in diabetes management* in Glucagon III, Handbook of Experimental Pharmacology, Lefevbre P J, Ed. Berlin, Springer Verlag, 1996,p. 311-326), effects which are glucose dependent (Kreymann, B., et al., Lancet ii: 1300-1304, 1987; Weir, G. C., et al., Diabetes 38:338-342, 1989). Moreover, it is also effective in patients with diabetes (Gutniak, M., N. Engl J Med 226:1316-1322, 1992; Nathan, D. M., et al., Diabetes Care 15:270-276, 1992), normalizing blood glucose levels in type 2 diabetic subjects (Nauck, M. A., et al., Diagbetologia 36:741-744, 1993), and improving glycemic control in type 1 patients (Creutzfeldt, W. O., et al., Diabetes Care 19:580-586, 1996), raising the possibility of its use as a therapeutic agent.

GLP-1 is, however, metabolically unstable, having a plasma half-life ($t_{1/2}$) of only 1-2 min in vivo. Exogenously administered GLP-1 is also rapidly degraded (Deacon, C. F., et al., Diabetes 44:1126-1131, 1995). This metabolic instability limits the therapeutic potential of native GLP-1. Hence, there is a need for GLP-1 analogues that are more active or are more metabolically stable than native GLP-1.

SUMMARY OF THE INVENTION

In one aspect, the present invention is directed to a compound of formula (I), $$(R^2R^3)\text{-}A^7\text{-}A^8\text{-}A^9\text{-}A^{10}\text{-}A^{11}\text{-}A^{12}\text{-}A^{13}\text{-}A^{14}\text{-}A^{15}\text{-}A^{16}\text{-}$$
$$A^{17}\text{-}A^{18}\text{-}A^{19}\text{-}A^{20}\text{-}A^{21}\text{-}A^{22}\text{-}A^{23}\text{-}A^{24}\text{-}A^{25}\text{-}A^{26}\text{-}$$
$$A^{27}\text{-}A^{28}\text{-}A^{29}\text{-}A^{30}\text{-}A^{31}\text{-}A^{32}\text{-}A^{33}\text{-}A^{34}\text{-}A^{35}\text{-}A^{36}\text{-}$$
$$A^{37}\text{-}A^{38}\text{-}A^{39}\text{-}R^1, \qquad (I)$$

wherein $A^7$ is L-His, Ura, Paa, Pta, Amp, Tma-His, des-amino-His, or deleted;

$A^8$ is Ala, D-Ala, Aib, Acc, N-Me-Ala, N-Me-D-Ala or N-Me-Gly;

$A^9$ is Glu, N-Me-Glu, N-Me-Asp or Asp;

$A^{10}$ is Gly, Acc, β-Ala or Aib;

$A^{11}$ is Thr or Ser;

$A^{12}$ is Phe, Acc, Aic, Aib, 3-Pal, 4-Pal, β-Nal, Cha, Trp or $X^1$-Phe;

$A^{13}$ is Thr or Ser;

$A^{14}$ is Ser or Aib;

$A^{15}$ is Asp or Glu;

$A^{16}$ is Val, Acc, Aib, Leu, Ile, Tle, Nle, Abu, Ala or Cha;

$A^{17}$ is Ser or Thr;

$A^{18}$ is Ser or Thr;

$A^{19}$ is Tyr, Cha, Phe, 3-Pal, 4-Pal, Acc, β-Nal or $X^1$-Phe;

$A^{20}$ is Leu, Acc, Aib, Nle, Ile, Cha, Tle, Val, Phe or $X^1$-Phe;

$A^{21}$ is Glu or Asp;

$A^{22}$ is Gly, Acc, β-Ala, Glu or Aib;

$A^{23}$ is Gln, Asp, Asn or Glu;

$A^{24}$ is Ala, Aib, Val, Abu, Tle or Acc;

$A^{25}$ is Ala, Aib, Val, Abu, Tle, Acc, Lys, Arg, hArg, Orn, HN—CH(($CH_2$)$_n$—N($R^{10}R^{11}$))—C(O) or HN—CH(($CH_2$)$_e$—$X^3$)—C(O);

$A^{26}$ is Lys, Arg, hArg, Orn, HN—CH(($CH_2$)$_n$—N($R^{10}R^{11}$))—C(O) or HN—CH(($CH_2$)$_e$—$X^3$)—C(O);

$A^{27}$ is Glu Asp, Leu, Aib or Lys;

$A^{28}$ is Phe, Pal, β-Nal, $X^1$-Phe, Aic, Acc, Aib, Cha or Trp;

$A^{29}$ is Ile, Acc, Aib, Leu, Nle, Cha, Tle, Val, Abu, Ala or Phe;

$A^{30}$ is Ala, Aib or Acc;

$A^{31}$ is Trp, β-Nal, 3-Pal, 4-Pal, Phe, Acc, Aib or Cha;

$A^{32}$ is Leu, Acc, Aib, Nle, Ile, Cha, Tle, Phe, $X^1$-Phe or Ala;

$A^{33}$ is Val, Acc, Aib, Leu, Ile, Tle, Nle, Cha, Ala, Phe, Abu, Lys or $X^1$-Phe;

$A^{34}$ is Lys, Arg, hArg, Orn, HN—CH(($CH_2)_n$—N($R^{10}R^{11}$))—C(O) or HN—CH(($CH_2)_e$—$X^3$)—C(O);

$A^{35}$ is Gly, β-Ala, D-Ala, Gaba, Ava, HN—$(CH_2)_m$—C(O), Aib, Acc or a D-amino acid;

$A^{36}$ is L- or D-Arg, D- or L-Lys, D- or L-hArg, D- or L-Orn, HN—CH(($CH_2)_n$—N($R^{10}R^{11}$))—C(O), HN—CH(($CH_2)_e$—$X^3$)—C(O) or deleted;

$A^{37}$ is Gly, β-Ala, Gaba, Ava, Aib, Acc, Ado, Arg, Asp, Aun, Aec, HN—$(CH_2)_m$—C(O), HN—CH(($CH_2)_n$—N($R^{10}R^{11}$))—C(O), a D-amino acid, or deleted;

$A^{38}$ is D- or L-Lys, D- or L-Arg, D- or L-hArg, D- or L-Orn, HN—CH(($CH_2)_n$—N($R^{10}R^{11}$))—C(O), HN—CH(($CH_2)_e$—$X^3$)—C(O) Ava, Ado, Aec or deleted;

$A^{39}$ is D- or L-Lys, D- or L-Arg, HN—CH(($CH_2)_n$—N($R^{10}R^{11}$))—C(O), Ava, Ado, or Aec; $X^1$ for each occurrence is independently selected from the group consisting of $(C_1-C_6)$alkyl, OH and halo;

$R^1$ is OH, $NH_2$, $(C_1-C_{30})$alkoxy, or NH—$X^2$—$CH_2$-$Z^0$, wherein $X^2$ is a $(C_1-C_{12})$hydrocarbon moiety, and $Z^0$ is H, OH, $CO_2H$ or $CONH_2$;

$X^3$ is,

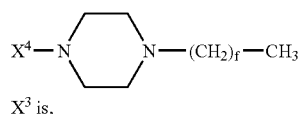

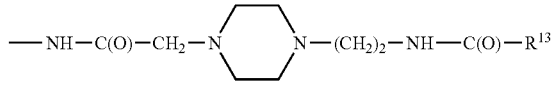

or —C(O)—$NHR^{12}$, wherein $X^4$ is, independently for each occurrence, —C(O)—, —NH—C(O)— or —$CH_2$—, and wherein f is, independently for each occurrence, an integer from 1 to 29 inclusive;

each of $R^2$ and $R^3$ is independently selected from the group consisting of H, $(C_1-C_{30})$alkyl, $(C_2-C_{30})$alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxyphenyl($C_1$-$C_{30}$)alkyl, and hydroxynaphthyl($C_1$-$C_{30}$)alkyl; or one of $R^2$ and $R^3$ is

$(C_1-C_{30})$acyl, $(C_1-C_{30})$alkylsulfonyl, $C(O)X^5$,

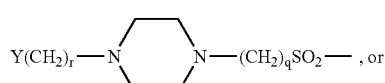

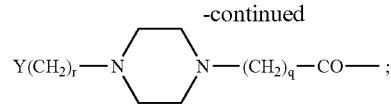

wherein Y is H, OH or $NH_2$; r is 0 to 4; q is 0 to 4;

and $X^5$ is $(C_1-C_{30})$alkyl, $(C_2-C_{30})$alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxyphenyl($C_1$-$C_{30}$)alkyl or hydroxynaphthyl($C_1$-$C_{30}$)alkyl;

e is, independently for each occurrence, an integer from 1 to 4 inclusive;

m is, independently for each occurrence, an integer from 5 to 24 inclusive;

n is, independently for each occurrence, an integer from 1 to 5, inclusive;

each of $R^{10}$ and $R^{11}$ is, independently for each occurrence, H, $(C_1-C_{30})$alkyl, $(C_1-C_{30})$acyl, $(C_1-C_{30})$alkylsulfonyl, —C((NH)($NH_2$)) or

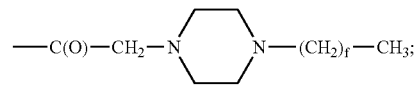

and $R^{12}$ and $R^{13}$ each is, independently for each occurrence, $(C_1-C_{30})$alkyl;

provided that:

when $A^7$ is Ura, Paa or Pta, then $R^2$ and $R^3$ are deleted;

when $R^{10}$ is $(C_1-C_{30})$acyl, —$(C_1-C_{30})$alkylsulfonyl, —C((NH)($NH_2$)) or

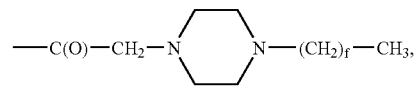

then $R^{11}$ is H or $(C_1-C_{30})$alkyl;

(i) at least one amino acid of a compound of formula (I) is not the same as the native sequence of hGLP-1(7-36,-37 or -38)$NH_2$ or hGLP-1(7-36,-37 or -38)OH;

(ii) a compound of formula (I) is not an analogue of hGLP-1(7-36,-37 or -38)$NH_2$ or hGLP-1(7-36,-37 or -38) OH wherein a single position has been substituted by Ala;

(iii) a compound of formula (I) is not ($Arg^{26,34}$, $Lys^{38}$) hGLP-1(7-38)-E, ($Lys^{26}$($N_ε$-alkanoyl))hGLP-1(7-36,-37 or -38)-E, ($Lys^{34}$($N_ε$-alkanoyl))hGLP-1(7-36,-37 or -38)-E, ($Lys^{26,34}$-bis($N_ε$-alkanoyl))hGLP-1(7-36,-37 or -38)-E, ($Arg^{26}$, $Lys^{34}$($N_ε$-alkanoyl))hGLP-1(8-36,-37 or -38)-E, ($Arg^{26,34}$, $Lys^{36}$($N_ε$-alkanoyl))hGLP-1(7-36,-37 or -38)-E or ($Arg^{26,34}$, $Lys^{38}$($N_ε$-alkanoyl))hGLP-1(7-38)-E, wherein E is —OH or —$NH_2$;

(iv) a compound of formula (I) is not $Z^1$-hGLP-1(7-36,-37 or -38)-OH, $Z^1$-hGLP-1(7-36,-37 or -38)-$NH_2$, wherein $Z^1$ is selected from the group consisting of:

(a) (Arg²⁶), (Arg³⁴), (Arg²⁶,³⁴), (Lys³⁶), (Arg²⁶, Lys³⁶), (Arg³⁴, Lys³⁶), (D-Lys³⁶), (Arg³⁶), (D-Arg³⁶), (Arg²⁶,³⁴, Lys³⁶) or (Arg²⁶,³⁶, Lys³⁴);

(b) (Asp²¹);

(c) at least one of (Aib⁸), (D-Ala⁸) and (Asp⁹); and (d) (Tyr⁷), (N-acyl-His⁷), (N-alkyl-His⁷), (N-acyl-D-His⁷) or (N-alkyl-D-His⁷);

(v) a compound of formula (I) is not a combination of any two of the substitutions listed in groups (a) to (d); and (vi) a compound of formula (I) is not (N-Me-Ala⁸)hGLP-1(8-36 or -37), (Glu¹⁵)hGLP-1(7-36 or -37), (Asp²¹)hGLP-1(7-36 or -37) or (Phe³¹)hGLP-1(7-36 or -37)

or a pharmaceutically acceptable salt thereof.

A preferred group of compounds of the immediately foregoing compound is where A¹¹ is Thr; A¹³ is Thr; A¹⁵ is Asp; A¹⁷ is Ser; A¹⁸ is Ser or Lys; A²¹ is Glu; A²³ is Gln or Glu; A²⁷ is Glu, Leu, Aib or Lys; and A³¹ is Trp, Phe or β-Nal; or a pharmaceutically acceptable salt thereof.

A preferred group of compounds of the immediately foregoing group of compounds is where A⁹ is Glu, N-Me-Glu or N-Me-Asp; A¹² is Phe, Acc, β-Nal or Aic; A¹⁶ is Val, Acc or Aib; A¹⁹ is Tyr or β-Nal; A²⁰ is Leu, Acc or Cha; A²⁴ is Ala, Aib or Acc; A²⁵ is Ala, Aib, Acc, Lys, Arg, hArg, Orn, HN—CH((CH₂)ₙ—N(R¹⁰R¹¹))—C(O) or HN—CH((CH₂)ₑ—X³)—C(O); A²⁸ is Phe or β-Nal; A²⁹ is Ile or Acc; A³⁰ is Ala or Aib; A³² is Leu, Acc or Cha; and A³³ is Val, Lys or Acc; or a pharmaceutically acceptable salt thereof.

A preferred group of compounds of the immediately foregoing group of compounds is where A⁸ is Ala, D-Ala, Aib, A6c, A5c, N-Me-Ala, N-Me-D-Ala or N-Me-Gly; A¹⁰ is Gly; A¹² is Phe, β-Nal, A6c or A5c; A¹⁶ is Val, A6c or A5c; A²⁰ is Leu, A6c, A5c or Cha; A²² is Gly, β-Ala, Glu or Aib; A²⁴ is Ala or Aib; A²⁹ is Ile, A6c or A5c; A³² is Leu, A6c, A5c or Cha; A³³ is Val, Lys, A6c or A5c; A³⁵ is Aib, β-Ala, Ado, A6c, A5c, D-Arg or Gly; and A³⁷ is Gly, Aib, β-Ala, Ado, D-Ala Ava, Asp, Aun, D-Asp, D-Arg, Aec, HN—CH((CH₂)ₙ—N(R¹⁰R¹¹))—C(O) or deleted; or a pharmaceutically acceptable salt thereof.

A preferred group of compounds of the immediately foregoing group of compounds is where X⁴ for each occurrence is —C(O)—; and R¹ is OH or NH₂; or a pharmaceutically acceptable salt thereof.

A preferred group of compounds of the immediately foregoing group of compounds or a pharmaceutically acceptable salt thereof is where R² is H and R³ is (C₁-C₃₀) alkyl, (C₂-C₃₀)alkenyl, (C₁-C₃₀)acyl, (C₁-C₃₀)alkylsulfonyl,

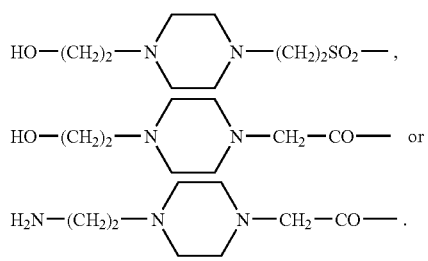

A preferred compound of the formula (I) is where A⁸ is Ala, D-Ala, Aib, A6c, A5c, N-Me-Ala, N-Me-D-Ala or N-Me-Gly; A¹⁰ is Gly; A¹² is Phe, β-Nal A6c or A5c; A¹⁶ is Val, A6c or A5c; A²⁰ is Leu, A6c, A5c or Cha; A²² is Gly, β-Ala, Glu or Aib; A²⁴ is Ala or Aib; A²⁹ is Ile, A6c or A5c; A³² is Leu, A6c, A5c or Cha; A³³ is Val, Lys, A6c or A5c;

A³⁵ is Aib, β-Ala, Ado, A6c, A5c D-Arg or Gly; and A³⁷ is Gly, Aib, β-Ala, Ado, D-Ala, Ava, Asp, Aun, D-Asp, D-Arg, Aec, HN—CH((CH₂)ₙ—N(R¹⁰R¹¹))—C(O) or deleted; X⁴ for each occurrence is —C(O)—; e for each occurrence is independently 1 or 2; R¹ is OH or NH₂; R¹⁰ is (C₁-C₃₀)acyl, (C₁-C₃₀)alkylsulfonyl or

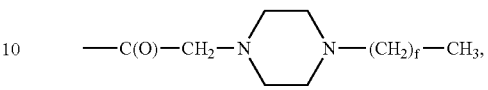

and R¹¹ is H; or a pharmaceutically acceptable salt thereof.

More preferred of the immediately foregoing compounds is where R¹⁰ is (C₄-C₂₀)acyl, (C₄-C₂₀)alkylsulfonyl or

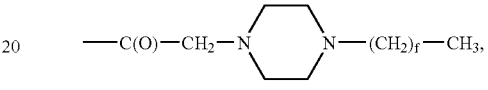

or a pharmaceutically acceptable salt thereof.

A more preferred compound of formula (I) is where said compound is of the formula:

(Aib⁸,³⁵)hGLP-1(7-36)NH₂, ((Nα-HEPES-His)⁷, Aib⁸,³⁵)hGLP-1(7-36)NH₂, ((Nα-HEPA-His)⁷, Aib⁸,³⁵)hGLP-1(7-36)NH₂, (Aib⁸, β-Ala³⁵)hGLP-1(7-36)NH₂, (Aib⁸,³⁵, Arg²⁶,³⁴, Lys³⁶(Nε-tetradecanoyl))hGLP-1(7-36)NH₂, (Aib⁸,³⁵, Arg²⁶, Lys³⁴(Nε-tetradecanoyl))hGLP-1(7-36)NH₂, (Aib⁸,³⁵,³⁷, Arg²⁶,³⁴, Lys³⁸(Nε-tetradecanoyl))hGLP-1(7-38)NH₂, (Aib⁸,³⁵, Arg²⁶,³⁴, Lys³⁶(Nε-decanoyl))hGLP-1(7-36)NH₂, (Aib⁸,³⁵, Arg²⁶,³⁴, Lys³⁶(Nε-dodecanesulfonyl))hGLP-1(7-36)NH₂, (Aib⁸,³⁵, Arg²⁶,³⁴, Lys³⁶(Nε-(2-(4-tetradecyl-1-piperazine)-acetyl)))hGLP-1(7-36)NH₂, (Aib⁸,³⁵, Arg²⁶,³⁴, Asp³⁶(1-(4-tetradecyl-piperazine)))hGLP-1(7-36)NH₂, (Aib⁸,³⁵, Arg²⁶,³⁴, Asp³⁶(1-tetradecylamino))hGLP-1(7-36)NH₂, (Aib⁸,³⁵, Arg²⁶,³⁴, Lys³⁶(Nε-tetradecanoyl),β-Ala³⁷)hGLP-1(7-37)-OH or (Aib⁸,³⁵, Arg²⁸,³⁴, Lys³⁶(Nε-tetradecanoyl))hGLP-1(7-36)-OH, or a pharmaceutically acceptable salt thereof.

More preferred of the immediately foregoing group of compounds is a compound of the formula:

(Aib⁸,³⁵)hGLP-1(7-36)NH₂, (Aib⁸, β-Ala³⁵)hGLP-1(7-36)NH₂, (Aib⁸,³⁵, Arg²⁶, Lys³⁴(Nε-tetradecanoyl))hGLP-1(7-36)NH₂, (Aib⁸,³⁵,³⁷, Arg²⁶,³⁴, Lys³⁸(Nε-tetradecanoyl))hGLP-1(7-38)NH₂, (Aib$^{8,35}$, Arg$^{26,34}$, Lys$^{36}$(N$_\epsilon$-decanoyl))hGLP-1(7-36)NH$_2$, or (Aib$^{8,35}$, Arg$^{26,34}$, Lys$^{36}$(N$_\epsilon$-tetradecanoyl),β-Ala$^{37}$)hGLP-1(7-37)—OH, or a pharmaceutically acceptable salt thereof.

Another more preferred compound of formula (I) is where said compound is of the formula:

(Aib$^{8,35}$, A6c$^{32}$)hGLP-1(7-36)NH$_2$;

(Aib$^{8,35}$, Glu$^{23}$)hGLP-1(7-36)NH$_2$;

(Aib$^{8,24,35}$)hGLP-1(7-36)NH$_2$;

(Aib$^{8,35}$, Glu$^{23}$, A6C$^{32}$)hGLP-1(7-36)NH$_2$;

(Aib$^8$, Glu$^{23}$, β-Ala$^{35}$)hGLP-1(7-36)NH$_2$;

(Aib$^{8,35}$, Arg$^{26,34}$)hGLP-1(7-36)NH$_2$;

(Aib$^{8,35}$, Arg$^{26,34}$, Lys$^{36}$(N$^\epsilon$-octanoyl))hGLP-1(7-36)NH$_2$;

(Aib$^{8,35}$, Arg$^{26,34}$, Lys$^{36}$(N$^\epsilon$-decanoyl))hGLP-1(7-36)OH;

(Aib$^{8,35}$, Lys$^{25}$, Arg$^{26,34}$, Lys$^{36}$(N$^\epsilon$-decanoyl))hGLP-1(7-36)OH;

(Aib$^8$, Arg$^{26,34}$, β-Ala$^{35}$, Lys$^{36}$(N$^\epsilon$-Aec-decanoyl))hGLP-1(7-36)NH$_2$;

(Aib$^{8,35}$, Arg$^{26,34}$, Ava$^{37}$, Ado$^{38}$)hGLP-1(7-38)NH$_2$;

(Aib$^{8,35}$, Arg$^{26,34}$, Asp$^{37}$, Ava$^{38}$, Ado$^{39}$)hGLP-1(7-39)NH$_2$;

(Aib$^{8,35}$, Arg$^{26,34}$, Aun$^{37}$)hGLP-1(7-37)NH$_2$;

(Aib$^{8,17,35}$,)hGLP-1(7-36)NH$_2$;

(Aib$^8$, Arg$^{26,34}$, β-Ala$^{35}$, D-Asp$^{37}$, Ava$^{38}$, Aun$^{39}$)hGLP-1(7-39)NH$_2$;

(Gly$^8$, β-Ala$^{35}$)hGLP-1(7-36)NH$_2$;

(Ser$^8$, β-Ala$^{35}$)hGLP-1(7-36)NH$_2$;

(Aib$^8$, Glu$^{22,23}$, β-Ala$^{35}$)hGLP-1(7-36)NH$_2$;

(Gly$^8$, Aib$^{35}$)hGLP-1(7-36)NH$_2$;

(Aib$^8$, Lys$^{18}$, β-Ala$^{35}$)hGLP-1(7-36)NH$_2$;

(Aib$^8$, Leu$^{27}$, β-Ala$^{35}$)hGLP-1(7-36)NH$_2$;

(Aib$^8$, Lys$^{33}$, β-Ala$^{35}$)hGLP-1(7-36)NH$_2$;

(Aib$^8$, Lys$^{18}$, Leu$^{27}$, β-Ala$^{35}$)hGLP-1(7-36)NH$_2$;

(Aib$^8$, D-Arg$^{36}$)hGLP-1(7-36)NH$_2$;

(Aib$^8$, β-Ala$^{35}$, D-Arg$^{37}$)hGLP-1(7-37)NH$_2$;

(Aib$^{8,27}$, β-Ala$^{35}$)hGLP-1(7-36)NH$_2$;

(Aib$^{8,27}$, β-Ala$^{35,37}$, Arg$^{38}$)hGLP-1(7-38)NH$_2$;

(Aib$^{8,27}$, β-Ala$^{35,37}$, Arg$^{38,39}$)hGLP-1(7-39)NH$_2$;

(Aib$^8$, Lys$^{18,27}$, β-Ala$^{35}$)hGLP-1(7-36)NH$_2$;

(Aib$^8$, Lys$^{27}$, β-Ala$^{35}$)hGLP-1(7-36)NH$_2$;

(Aib$^8$, β-Ala$^{35}$, Arg$^{38}$)hGLP-1(7-38)NH$_2$;

(Aib$^8$, Arg$^{26,34}$, β-Ala$^{35}$,)hGLP-1(7-36)NH$_2$;

(Aib$^8$, D-Arg$^{35}$)hGLP-1(7-36)NH$_2$;

(Aib$^8$, β-Ala$^{35}$, Arg$^{37}$)hGLP-1(7-37)NH$_2$;

(Aib$^8$, Phe$^{31}$, β-Ala$^{35}$)hGLP-1(7-36)NH$_2$;

(Aib$^{8,35}$, Phe$^{31}$)hGLP-1(7-36)NH$_2$;

(Aib$^{8,35}$, Nal$^{31}$)hGLP-1(7-36)NH$_2$;

(Aib$^{8,35}$, Nal$^{28,31}$)hGLP-1(7-36)NH$_2$;

(Aib$^{8,35}$, Arg$^{26,34}$, Nal$^{31}$)hGLP-1(7-36)NH$_2$;

(Aib$^{8,35}$, Arg$^{26,34}$, Phe$^{31}$)hGLP-1(7-36)NH$_2$;

(Aib$^{8,35}$, Nal$^{19,31}$)hGLP-1(7-36)NH$_2$;

(Aib$^{8,35}$, Nal$^{12,31}$)hGLP-1(7-36)NH$_2$;

(Aib$^{8,35}$, Lys$^{36}$(N$^\epsilon$-decanoyl))hGLP-1(7-36)NH$_2$;

(Aib$^{8,35}$, Arg$^{34}$, Lys$^{26}$(N$^\epsilon$-decanoyl))hGLP-1(7-36)NH$_2$;

(Aib$^{8,35}$, Arg$^{26,34}$, Lys$^{36}$(N$^\epsilon$-dodecanoyl))hGLP-1(7-36)NH$_2$;

(Aib$^8$, B-Ala$^{35}$, Ser$^{37}$(O-decanoyl))hGLP1(7-37)-NH$_2$;

(Aib$^{8,27}$, β-Ala$^{35,37}$, Arg$^{38}$, Lys$^{39}$(N$^\epsilon$-octanoyl))hGLP-1(7-39)NH$_2$;

(Aib$^8$, Arg$^{26,34}$, β-Ala$^{35}$, Lys$^{37}$(N$^\epsilon$-octanoyl))hGLP-1(7-37)NH$_2$;

(Aib$^8$, Arg$^{26,34}$, β-Ala$^{35}$, Lys$^{37}$(N$^\epsilon$-decanoyl))hGLP-1(7-37)NH$_2$; or (Aib$^8$, Arg$^{26,34}$, β-Ala$^{35}$, Lys$^{37}$(N$^\epsilon$-tetradecanoyl))hGLP-1(7-37)NH$_2$;

or a pharmaceutically acceptable salt thereof.

Another more preferred compound of formula (I) is each of the compounds that are specifically enumerated hereinbelow in the Examples section of the present disclosure, or a pharmaceutically acceptable salt thereof.

In another aspect, the present invention provides a pharmaceutical composition comprising an effective amount of a compound of formula (I) as defined hereinabove or a pharmaceutically acceptable salt thereof and a pharmaceutically acceptable carrier or diluent.

In yet another aspect, the present invention provides a method of eliciting an agonist effect from a GLP-1 receptor in a subject in need thereof which comprises administering to said subject an effective amount of a compound of formula (I) as defined hereinabove or a pharmaceutically acceptable salt thereof.

In a further aspect, the present invention provides a method of treating a disease selected from the group consisting of Type I diabetes, Type II diabetes, obesity, glucagonomas, secretory disorders of the airway, metabolic disorder, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake is desired, in a subject in need thereof which comprises administering to said subject an effective amount of a compound of formula (I) as defined hereinabove or a pharmaceutically acceptable salt thereof. A preferred method of the immediately foregoing method is where the disease being treated is Type I diabetes or Type II diabetes.

With the exception of the N-terminal amino acid, all abbreviations (e.g. Ala) of amino acids in this disclosure stand for the structure of —NH—CH(R)—CO—, wherein R is the side chain of an amino acid (e.g., CH$_3$ for Ala). For the N-terminal amino acid, the abbreviation stands for the structure of (R$^2$R$^3$)—N—CH(R)—CO—, wherein R is a side chain of an amino acid and R$^2$ and R$^3$ are as defined above, except when A$^7$ is Ura, Paa or Pta, in which case R$^2$ and R$^3$ are not present since Ura, Paa and Pta are considered here as des-amino amino acids. Amp, β-Nal, Nle, Cha, 3-Pal, 4-Pal and Aib are the abbreviations of the following α-amino acids: 4-amino-phenylalanine, β-(2-naphthyl)alanine, norleucine, cyclohexylalanine, β-(3-pyridinyl)alanine, β-(4-pyridinyl)alanine and α-aminoisobutyric acid, respectively. Other amino acid definitions are: Ura is urocanic acid; Pta is (4-pyridylthio) acetic acid; Paa is trans-3-(3-pyridyl) acrylic acid; Tma-His is N,N-tetramethylamidino-histidine; N-Me-Ala is N-methyl-alanine; N-Me-Gly is N-methyl-glycine; N-Me-Glu is N-methyl-glutamic acid; Tle is tert-butylglycine; Abu is α-aminobutyric acid; Tba is tert-butylalanine; Orn is ornithine; Aib is α-aminoisobutyric acid; β-Ala is β-alanine; Gaba is γ-aminobutyric acid; Ava is 5-aminovaleric acid; Ado is 12-aminododecanoic acid, Aic is 2-aminoindane-2-carboxylic acid; Aun is 11-aminoundecanoic acid; and Aec is 4-(2-aminoethyl)-1-carboxymethyl-piperazine, represented by the structure:

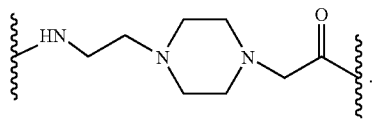

What is meant by Acc is an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c). In the above formula, hydroxyalkyl, hydroxyphenylalkyl, and hydroxynaphthylalkyl may contain 1-4 hydroxy substituents. $COX^5$ stands for $—C=O.X^5$. Examples of $—C=O.X^5$ include, but are not limited to, acetyl and phenylpropionyl.

What is meant by Lys($N_\epsilon$-alkanoyl) is represented by the following structure:

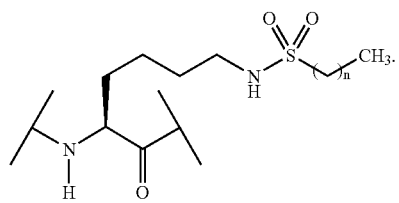

What is meant by Lys($N_\epsilon$-alkylsulfonyl) is represented by the following structure:

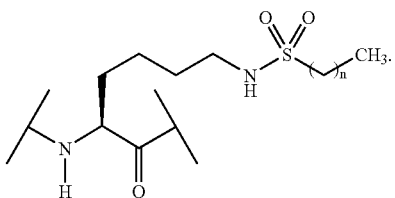

What is meant by Lys($N_\epsilon$-(2-(4-alkyl-1-piperazine)-acetyl)) is represented by the following structure:

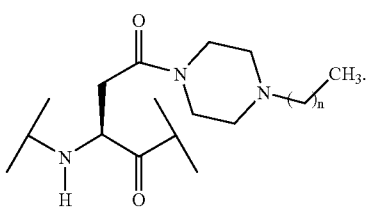

What is meant by Asp(1-(4-alkyl-piperazine)) is represented by the following structure:

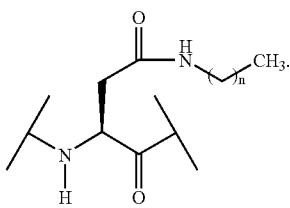

What is meant by Asp(1-alkylamino) is represented by the following structure:

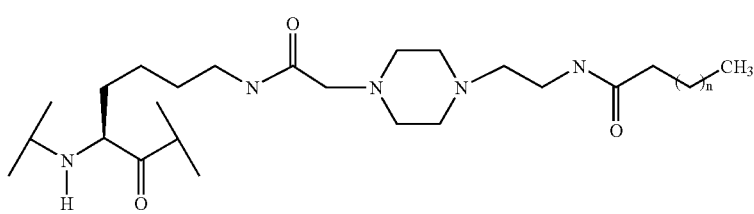

What is meant by Lys($N_\epsilon$-Aec-alkanoyl) is represented by the structure:

The variable n in the foregoing structures is 1-30. What is meant by Lys (Nε-ace-alkanoyl) is represented by the structure:

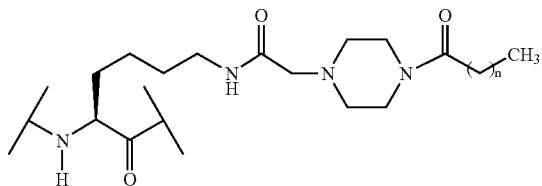

The full names for other abbreviations used herein are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2ClZ for 2-chlorobenzyloxycarbonyl, 2BrZ for 2-bromobenzyloxycarbonyl, OcHex for O-cyclohexyl, Fmoc for 9-fluorenylmethoxycarbonyl, HOBt for N-hydroxybenzotriazole and PAM resin for 4-hydroxymethylphenylacetamidomethyl resin.

The term "halo" encompasses fluoro, chloro, bromo and iodo.

The term "($C_1$-$C_{30}$)hydrocarbon moiety" encompasses alkyl, alkenyl and alkynyl, and in the case of alkenyl and alkynyl there are $C_2$-$C_{30}$.

A peptide of this invention is also denoted herein by another format, e.g., (A5c$^8$)hGLP-1(7-36)NH$_2$, with the substituted amino acids from the natural sequence placed between the first set of parentheses (e.g., A5c$^8$ for Ala$^8$ in hGLP-1). The abbreviation GLP-1 means glucagon-like peptide-1; hGLP-1 means human glucagon-like peptide-1. The numbers between the parentheses refer to the number of amino acids present in the peptide (e.g., hGLP-1(7-36) is amino acids 7 through 36 of the peptide sequence for human GLP-1). The sequence for hGLP-1(7-37) is listed in Mojsov, S., Int. J. Peptide Protein Res,. 40, 1992, pp. 333-342. The designation "NH$_2$" in hGLP-1(7-36)NH$_2$ indicates that the C-terminus of the peptide is amidated. hGLP-1(7-36) means that the C-terminus is the free acid. In hGLP-1(7-38), residues in positions 37 and 38 are Gly and Arg, respectively.

DETAILED DESCRIPTION

The peptides of this invention can be prepared by standard solid phase peptide synthesis. See, e.g., Stewart, J. M., et al., Solid Phase Synthesis (Pierce Chemical Co., 2d ed. 1984). The substituents $R^2$ and R3 of the above generic formula may be attached to the free amine of the N-terminal amino acid by standard methods known in the art. For example, alkyl groups, e.g., ($C_1$-$C_{30}$)alkyl, may be attached using reductive alkylation. Hydroxyalkyl groups, e.g., ($C_1$-$C_{30}$) hydroxyalkyl, may also be attached using reductive alkylation wherein the free hydroxy group is protected with a t-butyl ester. Acyl groups, e.g., COE$^1$, may be attached by coupling the free acid, e.g., E$^1$COOH, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^1$ is NH—$X^2$—CH$_2$—CONH$_2$, (i.e., $Z^0$=CONH$_2$), the synthesis of the peptide starts with BocHN—$X^2$—CH$_2$—COOH which is coupled to the MBHA resin. If $R^1$ is NH—$X^2$—CH$_2$—COOH, (i.e., $Z^0$=COOH) the synthesis of the peptide starts with Boc-HN—$X^2$—CH$_2$—COOH which is coupled to PAM resin. For this particular step, 4 molar equivalents of Boc-HN—$X^2$—COOH, HBTU and HOBt and 10 molar equivalents of DIEA are used. The coupling time is about 8 hours.

The protected amino acid 1-(N-tert-butoxycarbonylamino)-1-cyclohexanecarboxylic acid (Boc-A6c-OH) was synthesized as follows. 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 ml of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). The two organic layers were combined and washed with water (2×150 ml), dried over anhydrous MgSO$_4$, filtered, and concentrated to dryness under reduced pressure. The residue was recrystallized in ethyl acetate/hexanes. 9.2 g of the pure product was obtained. 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a GLP-1 analogue of this invention containing A5c, A6c and/or Aib, the coupling time is 2 hrs. for these residues and the residue immediately following them. For the synthesis of (Tma-His$^7$)hGLP-1(7-36)NH$_2$, HBTU (2 mmol) and DIEA (1.0 ml) in 4 ml DMF are used to react with the N-terminal free amine of the peptide-resin in the last coupling reaction; the coupling time is about 2 hours.

The substituents $R^2$ and $R^3$ of the above generic formula can be attached to the free amine of the N-terminal amino acid by standard methods known in the art. For example, alkyl groups, e.g., ($C_1$-$C_{30}$)alkyl, can be attached using reductive alkylation. Hydroxyalkyl groups, e.g., ($C_1$-$C_{30}$) hydroxyalkyl, can also be attached using reductive alkylation wherein the free hydroxy group is protected with a t-butyl ester. Acyl groups, e.g., COX$^1$, can be attached by coupling the free acid, e.g., X$^1$COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

A compound of the present invention can be tested for activity as a GLP-1 binding compound according to the following procedure.

Cell Culture:

RIN 5F rat insulinoma cells (ATCC-# CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidifed atmosphere of 5% CO$_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM ($^{125}$I)GLP-1(7-36) (~2200 Ci/mmol, New England Nuclear, Boston, Mass.), with and without 0.05 ml of unlabeled competing test peptides. After a 100 min incubation (25° C.), the bound ($^{125}$I)GLP-1(7-36) was separated from the free by rapid filtration through GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac L K B, Gaithersburg, Md.). Specific binding was defined as the total ($^{125}$I)GLP-1(7-36) bound minus that bound in the presence of 1000 nM GLP1(7-36) (Bachem, Torrence, Calif.).

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution for 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 is varied and multitudinous (See, Todd, J. F., et al., Clinical Science, 1998, 95, pp. 325-329; and Todd, J. F. et al., European Journal of Clinical Investigation, 1997, 27, pp.533-536). Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis, neurodegenerative diseases, renal failure, congestive heart failure, nephrotic syndrome, cirrhosis, pulmonary edema, hypertension, and disorders wherein the reduction of food intake is desired. GLP-1 analogues of the present invention that elicit an antagonist effect from a subject can be used for treating the following: hypoglycemia and malabsorption syndrome associated with gastroectomy or small bowel resection.

Accordingly, the present invention includes within its scope pharmaceutical compositions comprising, as an active ingredient, at least one of the compounds of formula (I) in association with a pharmaceutically acceptable carrier.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997,teaches polymeric sustained release compositions comprising a bioactive agent and chitosan. U.S. application Ser. No. 08/740,778 filed Nov. 1, 1996,teaches sustained release compositions comprising a bioactive agent and cyclodextrin. U.S. application Ser. No. 09/015,394 filed Jan. 29, 1998,teaches absorbable sustained release compositions of a bioactive agent. U.S. application Ser. No. 09/121,653 filed Jul. 23, 1998, teaches a process for making microparticles comprising a therapeutic agent such as a peptide in an oil-in-water process. U.S. application Ser. No. 09/131,472 filed Aug. 10, 1998, teaches complexes comprising a therapeutic agent such as a peptide and a phosphorylated polymer. U.S. application Ser. No. 09/184,413 filed Nov. 2, 1998, teaches complexes comprising a therapeutic agent such as a peptide and a polymer bearing a non-polymerizable lactone. The teachings of the foregoing patents and applications are incorporated herein by reference.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

The following examples describe synthetic methods for making a peptide of this invention, which methods are well-known to those skilled in the art. Other methods are also known to those skilled in the art. The examples are provided for the purpose of illustration and is not meant to limit the scope of the present invention in any manner.

Boc-βAla-OH, Boc-D-Arg(Tos)-OH and Boc-D-Asp (OcHex) were purchased from Nova Biochem, San Diego, Calif. Boc-Aun-OH was purchased from Bachem, King of Prussia, Pa. Boc-Ava-OH and Boc-Ado-OH were purchased from Chem-Impex International, Wood Dale, Ill. Boc-Nal-OH was purchased from Synthetech, Inc. Albany, Oreg.

EXAMPLE 1

$(Aib^{8,35})hGLP-1(7-36)NH_2$

The title peptide was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 90:180 (1992). 4-methylbenzhydrylamine (MBHA) resin (Peninsula, Belmont, Calif.) with the substitution of 0.91 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)-OH, Boc-Val-OH, Boc-Leu-OH, Boc-Gly-OH, Boc-Gln-OH, Boc-Ile-OH, Boc-Lys (2ClZ)-OH, Boc-Thr(Bzl)-OH, Boc-Ser(Bzl)-OH, Boc-Phe-OH, Boc-Aib-OH, Boc-Glu(OcHex)-OH and Boc-Trp (Fm)—OH. The synthesis was carried out on a 0.20 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min. except for the Boc-Aib-OH residues and the following residues, Boc-Lys(2ClZ)-OH and Boc-His(DNP)-OH wherein the coupling times were 2 hours.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min), the formyl group on the side chain of Trp was removed by treatment with a solution of 15% ethanolamine/15% water/70% DMF for 2×30 min. The peptide-resin was washed with DMF and DCM and dried under reduced pressure. The final cleavage was done by stirring the peptide-resin in 10 mL of HF containing 1 mL of anisole and dithiothreitol (24 mg) at 0° C. for 75 min. HF was removed by a flow of nitrogen. The residue was washed with ether (6×10 mL) and extracted with 4N HOAc (6×10 mL).

The peptide mixture in the aqueous extract was purified on reverse-phase preparative high pressure liquid chromatography (HPLC) using a reverse phase VYDAC® $C_{18}$ column (Nest Group, Southborough, Mass.). The column was eluted with a linear gradient (20% to 50% of solution B over 105 min.) at a flow rate of 10 mL/min (Solution A = water containing 0.1% TFA; Solution B=acetonitrile containing 0.1% of TFA). Fractions were collected and checked on analytical HPLC. Those containing pure product were combined and lyophilized to dryness. 135 mg of a white solid was obtained. Purity was 98.6% based on analytical HPLC analysis. Electro-spray mass spectrometer (MS (ES))S analysis gave the molecular weight at 3339.7 (in agreement with the calculated molecular weight of 3339.7).

EXAMPLE 2

$((N_\alpha\text{-HEPES-His})^7, Aib^{8,35})hGLP-1(7-36)NH_2$

The title compound (HEPES is (4-(2-hydroxyethyl)-1-piperazine-ethanesulfonic acid)) can be synthesized as follows: after assembly of the peptide $(Aib^{8,35})hGLP-1(7-36)NH_2$ on MBHA resin (0.20 mmol) according to the procedure of Example 1, the peptide-resin is treated with 100% TFA (2×2 min.) and washed with DMF and DCM. The resin is then neutralized with 10% DIEA in DMF for 2 min. After washing with DMF and DCM, the resin is treated with 0.23 mmol of 2-chloro-1-ethanesulfonyl chloride and 0.7 mmol of DIEA in DMF for about 1 hour. The resin is washed with DMF and DCM and treated with 1.2 mmol of 2-hydroxyethylpiperazine for about 2 hours. The resin is washed with DMF and DCM and treated with different reagents ((1) 20% mercaptoethanol/10% DIEA in DMF and (2) 15% ethanolamine/15% water/70% DMF) to remove the DNP group on the His side chain and formyl group on the Trp side chain as described above before the final HF cleavage of the peptide from the resin.

EXAMPLE 3

$((N_\alpha\text{-HEPA-His})^7, Aib^{8,35})hGLP-1(7-36)NH_2$

The title compound (HEPA is (4-(2-hydroxyethyl)-1-piperazineacetyl)) can be made substantially according to the procedure described in Example 2 for making ((N$_\alpha$-HEPES-His)$^7$, Aib$^{8,35}$)hGLP-1(7-36)NH$_2$ except that 2-bromoacetic anhydride is used in place of 2-chloro-1-ethanesulfonyl chloride.

EXAMPLE 4

(Aib$^8$, β-Ala$^{35}$)hGLP-1(7-36)NH$_2$

The title compound was synthesized substantially according to the procedure described for Example 1 using the appropriate protected amino acids. MS (ES) gave the molecular weight at 3325.7, calculated MW=3325.8, purity=99%, yield=85 mg.

The synthesis of other compounds of the present invention can be accomplished in substantially the same manner as the procedure described for the synthesis of (Aib$_{8,35}$)hGLP-1(7-36)NH$_2$ in Example 1 above, but using the appropriate protected amino acids depending on the desired peptide.

EXAMPLE 5

(Aib$^{8,35}$, Arg$^{26,34}$, Lys$^{36}$(N$_\epsilon$-tetradecanoyl))hGLP-1(7-36)NH$_2$ The Boc amino acids used were the same as those in the synthesis of (Aib$^{8,35}$)hGLP-1(7-36)NH$_2$ described in Example 1 except that Fmoc-Lys(Boc)-OH was used in this example. The first amino acid residue was coupled to the resin manually on a shaker. 2.5 mmol of Fmoc-Lys(Boc)-OH was dissolved in 4 mL of 0.5N HBTU in DMF. To the solution was added 1 mL of DIEA. The mixture was shaken for about 2 min. To the solution was then added 0.2 mmol of MBHA resin (substitution=0.91 mmol/g). The mixture was shaken for about 1 hr. The resin was washed with DMF and treated with 100% TFA for 2×2 min to remove the Boc protecting group. The resin was washed with DMF. Myristic acid (2.5 mmol) was pre-activated with HBTU (2.0 mmol) and DIEA (1.0 mL) in 4 mL of DMF for 2 min and was coupled to the Fmoc-Lys-resin. The coupling time was about 1 hr. The resin was washed with DMF and treated with 25% piperidine in DMF for 2×20 min to remove the Fmoc protecting group. The resin was washed with DMF and transferred to the reaction vessel of the peptide synthesizer. The following steps synthesis and purification procedures for the peptide were the same as those in the synthesis of (Aib$_{8,35}$)hGLP-1(7-36)NH$_2$ in Example 1. 43.1 mg of the title compound were obtained as a white solid. Purity was 98% based on analytical HPLC analysis. Electro-spray mass spectrometer analysis gave the molecular weight at 3577.7 in agreement with the calculated molecular weight 3578.7.

EXAMPLES 6-8

Examples 6-8 were synthesized substantially according to the procedure described for Example 5 using the appropriate protected amino acid and the appropriate acid in place of the Myristic acid used in Example 5.

EXAMPLE 6

(Aib$^{8,35}$, Arg$^{26}$, Lys$^{34}$(N$_\epsilon$-tetradecanoyl))hGLP-1(7-36)NH$_2$; Yield=89.6 mg; MS(ES)=3577.2, Calculated MW=3578.7; Purity 96%.

EXAMPLE 7

(Aib$^{8,35,37}$, Arg$^{26,34}$, Lys$^{38}$(N$_\epsilon$-tetradecanoyl))hGLP-1(7-38)NH$_2$; Yield=63.3 mg; MS(ES)=3818.7; Calculated MW=3819.5; Purity 96%.

EXAMPLE 8

(Aib$^{8,35}$, Arg$^{26,34}$, Lys$^{36}$(N$_\epsilon$-decanoyl))hGLP-1(7-36)NH$_2$; Yield=57.4 mg; MS(ES)=3521.5; Calculated MW=3522.7; Purity 98%; Acid=decanoic acid.

The syntheses of other compounds of the present invention containing Lys(N$_\epsilon$-alkanoyl) residue can be carried out in an analogous manner to the procedure described for Example 5, (Aib$^{8,35}$, Arg$^{26,34}$, Lys$^{36}$(N$_\epsilon$-tetradecanoyl))hGLP-1(7-36)NH$_2$. Fmoc-Lys(Boc)-OH amino acid is used for the residue of Lys(N$_\epsilon$-alkanoyl) in the peptide, while Boc-Lys(2ClZ)-OH amino acid is used for the residue of Lys. If the Lys(N$_\epsilon$-alkanoyl) residue is not at the C-terminus, the peptide fragment immediately prior to the Lys(N$_\epsilon$-alkanoyl) residue is assembled on the resin on the peptide synthesizer first. The appropriate acid corresponding to the desired alkanoyl can be purchased from Aldrich Chemical Co., Inc. Milwaukee, Wis., USA, e.g., octanoic acid, decanoic acid, lauric acid and palmitic acid.

EXAMPLE 9

(Aib$^{8,35}$, Arg$^{26,34}$, Lys$^{36}$(N$_\epsilon$-dodecanesulfonyl))hGLP-1(7-36)NH$_2$ The Boc amino acids to be used in this synthesis are the same as those used in the synthesis of Example 5. The first amino acid residue is coupled to the resin manually on a shaker. 2.5 mmol of Fmoc-Lys(Boc)-OH is dissolved in 4 mL of 0.5N HBTU in DMF. To the solution is added 1 mL of DIEA. The mixture is shaken for about 2 min. To the solution is then added 0.2 mmol of MBHA resin(substitution=0.91 mmol/g). The mixture is shaken for about 1 hr. The resin is washed with DMF and treated with 100% TFA for 2×2 min to remove the Boc protecting group. The resin is washed with DMF and to it is added 0.25 mmol of 1-dodecanesulfonyl chloride in 4 mL of DMF and 1 mL of DIEA. The mixture is shaken for about 2 hrs. The resin is washed with DMF and treated with 25% piperidine in DMF for 2×20 min to remove the Fmoc protecting group. The resin is washed with DMF and transferred to the reaction vessel of the peptide synthesizer. The synthesis of the rest of the peptide and purification procedures are the same as those described in Example 1.

The syntheses of other compounds of the present invention containing Lys(N$_\epsilon$-alkylsulfonyl) residue can be carried out in an analogous manner to the procedure described in Example 9. Fmoc-Lys(Boc)-OH amino acid is used for the residue of Lys(N$_\epsilon$-alkylsulfonyl) in the peptide, while Boc- Lys(2ClZ)-OH amino acid is used for the residue of Lys. If the Lys(N$_\epsilon$-alkylsulfonyl) residue is not at the C-terminus, the peptide fragment immediately prior to the Lys(N$_\epsilon$-alkylsulfonyl) residue is assembled on the resin on the peptide synthesizer first. The appropriate akylsulfonyl chloride can be obtained from Lancaster Synthesis Inc., Windham, N.H., USA, e.g., 1-octanesulfonyl chloride, 1-decanesulfonyl chloride, 1-dodecanesulfonyl chloride, 1-hexadecanesulfonyl chloride and 1-octadecylsulfonyl chloride.

EXAMPLE 10

(Aib$^{8,35}$, Arg$^{26,34}$, Lys$^{36}$(N$_\epsilon$-(2-(4-tetradecyl-1-piperazine)-acetyl)))hGLP-1(7-36)NH$_2$ The Boc amino acids to be used for this example are the same as those used in the synthesis of Example 5. The first amino acid residue is coupled to the resin manually on a shaker. 2.5 mmol of Fmoc-Lys(Boc)-OH is dissolved in 4 mL of 0.5N HBTU in DMF. To the solution is added 1 mL of DIEA. The mixture is shaken for about 2 min. To the solution is then added 0.2 mmol of MBHA (substitution=0.91 mmol/g) resin. The mixture is shaken for about 1 hr. The resin is washed with DMF and treated with 100% TFA for 2×2 min to remove the Boc protecting group. The resin is washed with DMF. The 2-bromoacetic acid (2.5 mmol) is pre-activated with HBTU (2.0 mmol) and DIEA (1 mL) in 4 mL of DMF for about 2 min and is added to the resin. The mixture is shaken for about 10 min and washed with DMF. The resin is then treated with 1.2 mmol of piperazine in 4 mL of DMF for about 2 hrs. The resin is washed with DMF and treated with 2 mmol of 1-iodotetradecane for about 4 hrs. After washing with DMF, the resin is treated with 3 mmol of acetic anhydride and 1 mL of DIEA in 4 mL of DMF for about 0.5 hr. The resin is washed with DMF and treated with 25% piperidine in DMF for 2×20 min. The resin is washed with DMF and transferred to the reaction vessel of the peptide synthesizer to continue the synthesis. The remaining synthesis and purification procedures for the peptide are the same as the procedures described for Example 1.

The syntheses of other compounds of the present invention containing Lys(N$_\epsilon$-(2-(4-alkyl-1-piperazine)-acetyl)) residue are carried out in an analogous manner as the procedure described for the synthesis of Example 10. Fmoc-Lys(Boc)-OH amino acid is used for the residue of Lys(N$_\epsilon$-(2-(4-alkyl-1-piperazine)-acetyl)) in the peptide, while Boc-Lys(2ClZ)-OH amino acid is used for the residue of Lys. The corresponding iodoalkane is used for the residue of Lys(N$_\epsilon$-(2-(4-alkyl-1-piperazine)-acetyl)) during the alkylation step. If the Lys(N$_\epsilon$-(2-(4-alkyl-1-piperazine)-acetyl)) residue is not at the C-terminus, the peptide fragment immediately prior to the Lys(N$_\epsilon$-(2-(4-alkyl-1-piperazine)-acetyl)) residue is assembled on the resin on the peptide synthesizer first.

EXAMPLE 11

(Aib$^{8,35}$, Arg$^{26,34}$, Asp$^{36}$(1-(4-tetradecyl-piperazine)))hGLP-1(7-36)NH$_2$ The Boc amino acids to be used in this example are the same as the amino acids used in synthesis of Example 5 except Fmoc-Asp(O-tBu)-OH is used at position 36. The first amino acid residue is coupled to the resin manually on a shaker. 2.5 mmol of Fmoc-Asp(O-tBu)-OH is dissolved in 4 mL of 0.5N HBTU in DMF. To the solution is added 1 mL of DIEA. The mixture is shaken for about 2 min. To the solution is then added 0.2 mmol of MBHA (substitution=0.91 mmol/g) resin. The mixture is shaken for about 1 hr. The resin is washed with DMF and treated with 100% TFA for 2×15 min to remove the tBu protecting group. The resin is washed with DMF and is treated with HBTU (0.6 mmol) and DIEA (1 mL) in 4 mL of DMF for about 15 min. 0.6 mmol of piperazine is added to the reaction mixture and the mixture is shaken for about 1 hr. The resin is washed with DMF and treated with 3 mmol of 1-iodotetradecane for about 4 hrs. After washing with DMF, the resin is treated with 3 mmol of acetic anhydride and 1 mL of DIEA in 4 mL of DMF for about 0.5 hr. The resin is washed with DMF and treated with 25% piperidine in DMF for 2×20 min to remove the Fmoc protecting group. The resin is washed with DMF and transferred to the reaction vessel of the peptide synthesizer to continue the synthesis. The remaining synthesis and purification procedures for the peptide are the same as those for the synthesis of Example 1.

The syntheses of other compounds of the present invention comprising Asp(1-(4-alkylpiperazine)) or Glu(1-(4-alkylpiperazine)) residue are carried out in an analogous manner as the procedure described for the synthesis of Example 11. Fmoc-Asp(O-tBu)-OH or Fmoc-Glu(O-tBu)-OH amino acid is used for the residue of Asp(1-(4-alkylpiperazine)) or Glu(1-(4-alkylpiperazine)) in the peptide, while Boc-Asp(OcHex)-OH or Boc-Glu(OcHex)-OH amino acid is used for the residue of Asp or Glu. The corresponding iodoalkane is used for the residue of Lys(N$_\epsilon$-(2-(4-alkyl-1-piperazine)-acetyl)) during the alkylation step. If the Asp(1-(4-alkylpiperazine)) or Glu(1-(4-alkylpiperazine)) residue is not at the C-terminus, the peptide fragment immediately prior to the Asp(1-(4-alkylpiperazine)) or Glu(1-(4-alkylpiperazine)) residue is assembled on the resin on the peptide synthesizer first.

EXAMPLE 12

(Aib$^{8,35}$, Arg$^{26,34}$, Asp$^{36}$(1-tetradecylamino))hGLP-1(7-36)NH$_2$

The Boc amino acids to be used for this example are the same as those used in Example 5. The first amino acid residue is coupled to the resin manually on a shaker. 2.5 mmol of Fmoc-Asp(O-tBu)-OH is dissolved in 4 mL of 0.5N HBTU in DMF. To the solution is added 1 mL of DIEA. The mixture is shaken for about 2 min. To the solution is then added 0.2 mmol of MBHA (substitution=0.91 mmol/g) resin. The mixture is shaken for about 1 hr. The resin is washed with DMF and treated with 100% TFA for 2×15 min to remove the t-Bu protecting group. The resin is washed with DMF and is treated with HBTU (0.6 mmol) and DIEA (1 mL) in 4 mL of DMF for about 15 min. 0.6 mmol of 1-tetradecaneamine is added to the reaction mixture and the mixture is shaken for about 1 hr. The resin is washed with DMF and treated with 25% piperidine in DMF for 2×20 min to remove the Fmoc protecting group. The resin is washed with DMF and transferred to the reaction vessel of the peptide synthesizer to continue the synthesis. The remaining synthesis and purification procedures for the peptide of this example are the same as those described for the synthesis of Example 1.

The syntheses of other compounds of the present invention containing Asp(1-alkylamino) or Glu(1-alkylamino) residue are carried out in an analogous manner as described for the synthesis of Example 12. Fmoc-Asp(O-tBu)-OH or Fmoc-Glu(O-tBu)-OH amino acid is used for the residue of Asp(1-alkylamino) or Glu(1-alkylamino), respectively, in the peptide, while Boc-Asp(OcHex)-OH or Boc-Glu (OcHex)-OH amino acid is used for the residue of Asp or Glu, respectively. If the Asp(1-alkylamino) or Glu(1-alkylamino) residue is not at the C-terminus, the peptide fragment immediately prior to the Asp(1-alkylamino) or Glu(1-alkylamino) residue is assembled on the resin on the peptide synthesizer first.

EXAMPLE 13

(Aib$^{8,35}$, Arg$^{26,34}$, Lys$^{36}$(N$_\epsilon$-tetradecanoyl),β-Ala$^{37}$) hGLP-1(7-37)-OH The Boc amino acids used are the same as those in the synthesis of (Aib$^{8,35}$, Arg$^{26,34}$, Lys$^{36}$(N$_\epsilon$-tetradecanoyl)) hGLP-1(7-36)NH$_2$ (Example 5). 270 mg of Boc-β-Ala-PAM resin (Novabiochem, San Diego, Calif., substitution=0.74 mmol/g) was used. The Boc protecting group on Boc-β-Ala-PAM resin was deblocked on a shaker with 100% TFA for 2×2 min first. The remainder of the synthesis and purification procedures were the same as that in Example 5. 83.0 mg of the title peptide was obtained as white solid. Purity was 99% based on analytical HPLC analysis. Electro-spray mass spectrometer analysis gave the molecular weight at 3650.5 in agreement with the calculated weight 3650.8.

EXAMPLE 14

(Aib$^{8,35}$, Arg$^{26,34}$, Lys$^{36}$(N$_\epsilon$-tetradecanoyl))hGLP-1 (7-36)-OH The Boc amino acids to be used are the same as those in the synthesis of (Aib$^{8,35}$, Arg$^{26,34}$, Lys$_{36}$(N$_\epsilon$-tetradecanoyl)) hGLP-1(7-36)NH$_2$ (Example 5). Fmoc-Lys(Boc)-OH (2.5 mmol) is pre-activated with HBTU (2.0 mmol), HOBt (2.0 mmol and DIEA (2.5 ml) in DMF (4 ml) for about 2 min. This amino acid is coupled to 235 mg of PAM resin (Chem-Impex, Wood Dale, Ill.; substitution=0.85 mmol/g) manually on a shaker. The coupling time is about 8 hrs. The remainder of the synthesis and purification procedures are the same as those in Example 5. Electro-spray mass spectrometer analysis gave the molecular weight at 3579.15 in agreement with the calculated weight 3579.5.

The syntheses of other analogs of hGLP-1(7-36)-OH, hGLP-1(7-37)-OH and hGLP-1(7-38)-OH of the instant invention which contain Lys(N$_\epsilon$-alkanoyl) residue can be carried out in an analogous manner according to the procedure described for the synthesis of Example 14. Fmoc-Lys (Boc)-OH amino acid is used for the residue of Lys(N$_\epsilon$-alkanoyl) in the peptide, while Boc-Lys(2ClZ)-OH amino acid is used for the residue of Lys.

EXAMPLE 366

(Aib$^8$, β-Ala$^{35}$, Aec$^{37}$)hGLP-1(7-37)NH$_2$

A mixture of MBHA resin (0.2 mmol, substitution=0.91 mmol/g), Fmoc-Aec-OH (0.40 g, 0.829 mmol), HBTU (1.5 mL @ 0.5M in DMF) and DIEA (0.5 mL) in a reaction vessel was shaken on a shaker for 4 h at room temperature. The resin was then washed with DMF and treated with 25% piperidine in DMF for 2×20 min. The resin was washed with DMF and DCM and transferred to the reaction vessel of the peptide synthesizer to continue the assembly of the rest of the peptide according the procedure described for Example 1. The purification procedure was also the same as the one described in Example 1. Electro-spry mass spectrometer analysis gave the molecular weight at 3494.8 in agreement with the calculated molecular weight 3494.99. Purity 93%; Yield 79.1 mg.

EXAMPLE 367

(Aib$^8$, β-Ala$^{35}$, Aec$^{38}$)hGLP-1(7-38)NH$_2$

Example 367 was synthesized substantially according to the procedure described for Example 366. MS(ES)=3551.7, calculated MW=3552.04; Purity 97%; Yield 97.4 mg.

EXAMPLE 368

(Aib$^8$, β-Ala$^{35}$, Aec$^{37,38}$)hGLP-1(7-38)NH$_2$

A mixture of MBHA resin (0.2 mmol, substitution=0.91 mmol/g), Fmoc-Aec-OH (0.289 g, 0.6 mmol), HBTU (1.12 mL @ 0.5M in DMF) and DIEA (0.4 mL) in a reaction vessel was shaken on a shaker for 2 h at room temperature. The resin was then washed with DMF and treated with 30% piperidine in DMF for 2×15 min. The resin was washed with DMF. To the reaction vessel were added Fmoc-Aec-OH (0.289 g, 0.6 mmol), HBTU (1.12 mL @ 0.5M in DMF) and DIEA (0.4 mL). The mixture was shaken at room temperature for 2 h. The resin was washed with DMF and treated with 30% piperidine in DMF for 2×15 min. The resin was washed with DMF and DCM and transferred to the reaction vessel of the peptide synthesizer to continue the assembly of the rest of the peptide according the procedure described for Example 1. The purification procedure was also the same as the one described in Example 1. Electro-spry mass spectrometer analysis gave the molecular weight at 3663.9 in agreement with the calculated molecular weight 3664.26. Purity 100%; Yield 75.3 mg.

EXAMPLE 369

(Aib$^8$, Arg$^{26,34}$, β-Ala$^{35}$, Lys$^{36}$(N$^\epsilon$-Aec-decanoyl)) hGLP-1(7-36)NH$_2$ A mixture of MBHA resin (0.2 mmol, substitution=0.91 mmol/g), Boc-Lys(Fmoc)-OH (1.17 g, 2.5 mmol), HBTU (4 mL @ 0.5M in DMF) and DIEA (1 mL) in a reaction vessel was shaken on a shaker at room temperature for 10 min. The resin was washed with DMF and treated with 25% piperidine in DMF for 2×15 min. The resin was washed with DMF. To the reaction vessel were added Fmoc-Aec-OH (0.289 g, 0.6 mmol), HBTU (1.12 mL @ 0.5M in DMF) and DIEA (0.4 mL). The mixture was shaken at room temperature for 10 min. The resin was washed with DMF and treated with 30% piperidine in DMF for 2×15 min. The resin was washed with DMF and treated with a mixture of decanoic acid (431 mg, 2.5 mmol), HBTU (4 mL @ 0.5M in DMF) and DIEA (1 mL) for 10 min. The resin was washed with DMF and treated with 100% TFA for 2×2 min. The resin was washed with DMF and DCM and transferred to the reaction vessel of the peptide synthesizer to continue the assembly of the rest of the peptide according the procedure described for Example 1. The purification procedure was also the same as the one described in Example 1. Electro-spry mass spectrometer analysis gave the molecular weight at 3677.0 in agreement with the calculated molecular weight 3677.25. Purity 97.6%; Yield 44.8 mg.

The following examples can be made according to the appropriate procedures described hereinabove.

EXAMPLE 15:

(Aib$^{35}$)hGLP-1(7-36)NH$_2$

EXAMPLE 16

(β-Ala$^{35}$)hGLP-1(7-36)NH$_2$

EXAMPLE 17

((N$^\alpha$-Me-His)$^7$, Aib$^{8,35}$)hGLP-1(7-36)NH$_2$

EXAMPLE 18

((N$^\alpha$-Me-His)$^7$, Aib$^8$, β-Ala$^{35}$)hGLP-1(7-36)NH$_2$

EXAMPLE 19

((N$^\alpha$-Me-His)$^7$, Aib$^{8,35}$, Arg$^{26,34}$)hGLP-1(7-36)NH$_2$

EXAMPLE 20

((N$^\alpha$-Me-His)$^7$, Aib$^8$, Arg$^{26,34}$, β-Ala$^{35}$)hGLP-1(7-36)NH$_2$

EXAMPLE 21

(Aib$^8$, A6c$^{35}$)hGLP-1(7-36)NH$_2$

EXAMPLE 22

(Aib$^8$, A5c$^{35}$)hGLP-1(7-36)NH$_2$

EXAMPLE 23

(Aib$^8$, D-Ala$^{35}$)hGLP-1(7-36)NH$_2$

EXAMPLE 24

(Aib$^{8,35}$, A6c$^{32}$)hGLP-1(7-36)NH$_2$

EXAMPLE 25

(Aib$^{8,35}$, A5c$^{32}$)hGLP-1(7-36)NH$_2$

EXAMPLE 26

(Aib$^{8,35}$, Glu$^{23}$)hGLP-1(7-36)NH$_2$

EXAMPLE 27

(Aib 8,24,35)hGLP-1(7-36)NH$_2$

EXAMPLE 28

(Aib$^{8,30,35}$)hGLP-1(7-36)NH$_2$

EXAMPLE 29

(Aib$^{8,25,35}$)hGLP-1(7-36)NH$_2$

EXAMPLE 30

(Aib$^{8,35}$, A6c$^{16,20}$)hGLP-1(7-36)NH$_2$

EXAMPLE 31

(Aib$^{8,35}$, A6c$^{16,29,32}$)hGLP-1(7-36)NH$_2$

EXAMPLE 32

(Aib$^{8,35}$, A6c$^{20,32}$)hGLP-1(7-36)NH$_2$

EXAMPLE 33

(Aib$^{8,35}$, A6c$^{20}$)hGLP-1(7-36)NH$_2$

EXAMPLE 34

(Aib$^{8,35}$, Lys$^{25}$)hGLP-1(7-36)NH$_2$

EXAMPLE 35

(Aib$^{8,24,35}$, A6c$^{20}$)hGLP-1(7-36)NH$_2$

EXAMPLE 36

(Aib$^{8,35}$, A6c$^{29,32}$)hGLP-1(7-36)NH$_2$

EXAMPLE 37

(Aib$^{8,24,35}$, A6c$^{29,32}$)hGLP-1(7-36)NH$_2$

EXAMPLE 38

(Aib$^{8,35}$, A6c$^{12}$)hGLP-1(7-36)NH$_2$

EXAMPLE 39

(Aib$^{8,35}$, Cha$^{20}$)hGLP-1(7-36)NH$_2$

EXAMPLE 40

(Aib$^{8,35}$, A6c$^{33}$)hGLP-1(7-36)NH$_2$

EXAMPLE 41

(Aib$^{8,35}$, A6c$^{20,32}$)hGLP-1(7-36)NH$_2$

EXAMPLE 42

(Aib$^8$, A6c$^{16,20}$, β-Ala$^{35}$)hGLP-1(7-36)NH$_2$

EXAMPLE 43

(Aib$^{8,35}$, β-Ala$^{22}$)hGLP-1(7-36)NH$_2$

EXAMPLE 44

(Aib$^{8,22,35}$)hGLP-1(7-36)NH$_2$

EXAMPLE 45

(Aib$^{8,35}$, Glu$^{23}$, A6c$^{32}$)hGLP-1(7-36)NH$_2$

EXAMPLE 46

(Aib$^{8,24,35}$, Glu$^{23}$, A6c$^{32}$)hGLP-1(7-36)NH$_2$

EXAMPLE 47

(Aib$^{8,24,25,35}$, Glu$^{23}$, A6c$^{32}$)hGLP-1(7-36)NH$_2$

EXAMPLE 48

(Aib$^{8,24,25,35}$, A6c$^{16,20,32}$, Glu$^{23}$)hGLP-1(7-36)NH$_2$

EXAMPLE 49

(Aib$^8$, A6c$^{32}$, β-Ala$^{35}$)hGLP-1(7-36)NH$_2$

EXAMPLE 50

(Aib$^8$, A5c$^{32}$, β-Ala$^{35}$)hGLP-1(7-36)NH$_2$

EXAMPLE 51

(Aib$^8$, Glu$^{23}$, β-Ala$^{35}$)hGLP-1(7-36)NH$_2$

EXAMPLE 52

(Aib$^{8,24}$, β-Ala$^{35}$)hGLP-1(7-36)NH$_2$

EXAMPLE 53

(Aib$^{8,30}$, β-Ala$^{35}$)hGLP-1(7-36)NH$_2$

EXAMPLE 54

(Aib$^{8,25}$, β-Ala$^{35}$)hGLP-1(7-36)NH$_2$

EXAMPLE 55

(Aib$^8$, A6c$^{16,20}$, β-Ala$^{35}$)hGLP-1(7-36)NH$_2$

EXAMPLE 56

(Aib$^8$, A6c$^{16,29,32}$, β-Ala$^{35}$)hGLP-1(7-36)NH$_2$

EXAMPLE 57

(Aib$^8$, A6c$^{20,32}$, β-Ala$^{35}$)hGLP-1(7-36)NH$_2$

EXAMPLE 58

(Aib$^8$, A6c$^{20}$, β-Ala$^{35}$)hGLP-1(7-36)NH$_2$

EXAMPLE 59

(Aib$^8$, Lys$^{25}$, β-Ala$^{35}$)hGLP-1(7-36)NH$_2$

EXAMPLE 60

(Aib$^{8,24}$, A6c$^{20}$, β-Ala$^{35}$)hGLP-1(7-36)NH$_2$

EXAMPLE 61

(Aib$^8$, A6c$^{29,32}$, β-Ala$^{35}$)hGLP-1(7-36)NH$_2$

EXAMPLE 62

(Aib$^{8,24}$, A6c$^{29,32}$, β-Ala$^{35}$)hGLP-1(7-36)NH$_2$

EXAMPLE 63

(Aib$^8$, A6c$^{12}$, β-Ala$^{35}$)hGLP-1(7-36)NH$_2$

EXAMPLE 64

(Aib$^8$, Cha$^{20}$, β-Ala$^{35}$)hGLP-1(7-36)NH$_2$

EXAMPLE 65

(Aib$^8$, A6c$^{33}$, β-Ala$^{35}$)hGLP-1(7-36)NH$_2$

EXAMPLE 66

(Aib$^8$, A6c$^{20,32}$, β-Ala$^{35}$)hGLP-1(7-36)NH$_2$

EXAMPLE 67

(Aib$^8$, β-Ala$^{22,35}$)hGLP-1(7-36)NH$_2$

EXAMPLE 68

(Aib$^{8,22}$, β-Ala$^{35}$)hGLP-1(7-36)NH$_2$

EXAMPLE 69

(Aib$^8$, Glu$^{23}$, A6c$^{32}$, β-Ala$^{35}$)hGLP-1(7-36)NH$_2$

EXAMPLE 70

(Aib$^{8,24}$, Glu$^{23}$, A6c$^{32}$, β-Ala$^{35}$)hGLP-1(7-36)NH$_2$

EXAMPLE 71

(Aib$^{8,24}$, Glu$^{23}$, A6c$^{32}$, Lys$^{34}$(N$_\epsilon$-octanoyl), β-Ala$^{35}$)hGLP-1(7-36)NH$_2$

EXAMPLE 72

(Aib$^{8,24,25}$, Glu$^{23}$, A6c$^{32}$, β-Ala$^{35}$)hGLP-1(7-36)NH$_2$

EXAMPLE 73

(Aib$^{8,24,25}$, A6c$^{16,20,32}$, Glu$^{23}$, β-Ala$^{35}$)hGLP-1(7-36)NH$_2$

EXAMPLE 74

(Aib$^{8,35}$, D-Arg$^{36}$)hGLP-1(7-36)NH$_2$

EXAMPLE 75

(Aib$^{8,35}$, D-Lys$^{36}$)hGLP-1(7-36)NH$_2$

EXAMPLE 76

(Aib$^8$, β-Ala$^{35}$, D-Arg$^{36}$)hGLP-1(7-36)NH$_2$

EXAMPLE 77

(Aib$^8$, β-Ala$^{35}$, D-Lys$^{36}$)hGLP-1(7-36)NH$_2$

EXAMPLE 78

(Aib$^{8,35}$, Arg$^{26,34}$)hGLP-1(7-36)NH$_2$

EXAMPLE 79

(Aib$^8$, Arg$^{26,34}$, β-Ala$^{35}$)hGLP-1(7-36)NH$_2$

EXAMPLE 80

(Aib$^{8,35}$, Arg$^{25,26,34}$)hGLP-1(7-36)NH$_2$

EXAMPLE 81

(Aib$^8$, Arg$^{25,26,34}$, β-Ala$^{35}$)hGLP-1(7-36)NH$_2$

EXAMPLE 82

(Aib$^8$, Arg$^{26,34}$, β-Ala$^{35}$, Lys$^{36}$(N$^\epsilon$-tetradecanoyl))hGLP-1(7-36)OH

EXAMPLE 83

(Aib$^{8,35}$, Arg$^{26,34}$, Lys$^{36}$(N$^\epsilon$-tetradecanoyl))hGLP-1(7-37)OH

EXAMPLE 84

(Aib$^{8,35,37}$, Arg$^{26,34}$, Lys$^{36}$(N$^\epsilon$-tetradecanoyl))hGLP-1(7-37)OH

EXAMPLE 85

(Aib$^{8,35}$, Arg$^{26,34}$, Lys$^{36}$(N$^\epsilon$-tetradecanoyl), D-Ala$^{37}$)hGLP-1(7-37)OH

EXAMPLE 86

(Aib$^{8,35,37}$, Arg$^{26,34}$, Lys$^{38}$(N$^\epsilon$-tetradecanoyl))hGLP-1(7-38)OH

EXAMPLE 87

(Aib$^{8,35}$, Arg$^{26,34}$, β-Ala$^{37}$, Lys$^{38}$(N$^\epsilon$-tetradecanoyl))hGLP-1(7-38)OH

EXAMPLE 88

(Aib$^{8,35}$, Arg$^{26,34}$, Lys$^{38}$(N$^\epsilon$-tetradecanoyl))hGLP-1(7-38)OH

EXAMPLE 89

(Aib$^8$, Arg$^{26,34}$, Lys$^{36}$(N$^\epsilon$-tetradecanoyl), β-Ala$^{37}$)hGLP-1(7-37)OH

EXAMPLE 90

(Aib$^{8,37}$, Arg$^{26,34}$, Lys$^{36}$(N$^\epsilon$-tetradecanoyl))hGLP-1(7-37)OH

EXAMPLE 91

(Aib$^{8,35}$, Arg$^{26,34}$, Ado$^{37}$)hGLP-1(7-37)OH

EXAMPLE 92

(Aib$^{8,35}$, Arg$^{26,34}$, Ado$^{37}$)hGLP-1(7-37)NH$_2$

EXAMPLE 93

(Aib$^8$, Arg$^{26,34}$, Lys$^{36}$(N$^\epsilon$-tetradecanoyl), D-Ala$^{37}$)hGLP-1(7-37)OH

EXAMPLE 94

(Aib$^{8,37}$, Arg$^{26,34}$, Lys$^{38}$(N$^\epsilon$-tetradecanoyl))hGLP-1(7-38)OH

EXAMPLE 95

(Aib$^8$, Arg$^{26,34}$, β-Ala$^{37}$, Lys$^{38}$(N$^\epsilon$-tetradecanoyl))hGLP-1(7-38)OH

EXAMPLE 96

(Aib$^{8,35}$, Lys$^{26}$(N$^\epsilon$-octanoyl))hGLP-1(7-36)NH$_2$

EXAMPLE 97

(Aib$^{8,35}$, Lys$^{26}$(N$^\epsilon$-tetradecanoyl))hGLP-1(7-36)NH$_2$

EXAMPLE 98

(Aib$^{8,35}$, Lys$^{26}$(N$^\epsilon$-hexadecanoyl))hGLP-1(7-36)NH$_2$

EXAMPLE 99

(Aib$^8$, Lys$^{26}$(N$^\epsilon$-octanoyl), β-Ala$^{35}$)hGLP-1(7-36)NH$_2$

EXAMPLE 100

(Aib$^8$, Lys$^{26}$(N$^\epsilon$-tetradecanoyl), β-Ala$^{35}$)hGLP-1(7-36)NH$_2$

EXAMPLE 101

(Aib$^8$, Lys$^{26}$(N$^\epsilon$-hexadecanoyl), β-Ala$^{35}$)hGLP-1(7-36)NH$_2$

EXAMPLE 102

(Aib$^{8,35}$, Lys$^{26}$(N$^\epsilon$-octanoyl), Arg$^{34}$)hGLP-1(7-36)NH$_2$

EXAMPLE 103

(Aib$^{8,35}$, Lys$^{26}$(N$^\epsilon$-tetradecanoyl), Arg$^{34}$)hGLP-1(7-36)NH$_2$

EXAMPLE 104

(Aib$^{8,35}$, Lys$^{26}$(N$^\epsilon$-hexadecanoyl), Arg$^{35}$)hGLP-1(7-36)NH$_2$

EXAMPLE 105

(Aib$^{8,35}$, Lys$^{26}$(N$^\epsilon$-decanoyl), Arg$^{34}$)hGLP-1(7-36)NH$_2$

EXAMPLE 106

(Aib$^{8,35}$, Lys$^{25}$, Lys$^{26}$(N$^\epsilon$-octanoyl), Arg$^{35}$)hGLP-1(7-36)NH$_2$

EXAMPLE 107

(Aib$^{8,35}$, Lys$^{25}$, Lys$^{26}$(N$^\epsilon$-tetradecanoyl), Arg$^{34}$)hGLP-1(7-36)NH$_2$

EXAMPLE 108

(Aib$^{8,35}$, Lys$^{25}$, Lys$^{26}$(N$^\epsilon$-hexadecanoyl), Arg$^{34}$)hGLP-1(7-36)NH$_2$

EXAMPLE 109

(Aib$^{8,35}$, Arg$^{25,34}$, Lys$^{26}$(N$^\epsilon$-octanoyl))hGLP-1(7-36)NH$_2$

EXAMPLE 110

(Aib$^{8,35}$, Arg$^{25,34}$, Lys$^{26}$(N$^\epsilon$-tetradecanoyl))hGLP-1(7-36)NH$_2$

EXAMPLE 111

(Aib$^{8,35}$, Arg$^{25,34}$, Lys$^{26}$(N$^\epsilon$-hexadecanoyl))hGLP-1(7-36)NH$_2$

EXAMPLE 112

(Aib$^{8,35}$, Arg$^{25,34}$, Lys$^{28}$(N$^\epsilon$-decanoyl))hGLP-1(7-36)NH$_2$

EXAMPLE 113

(Aib$^{8}$, Lys$^{26}$(N$^\epsilon$-octanoyl), Arg$^{34}$, β-Ala$^{35}$)hGLP-1(7-36)NH$_2$

EXAMPLE 114

(Aib$^{8}$, Lys$^{26}$(N$^\epsilon$-tetradecanoyl), Arg$^{34}$, β-Ala$^{35}$)hGLP-1(7-36)NH$_2$

EXAMPLE 115

(Aib$^{8}$, Lys$^{26}$(N$^\epsilon$-hexadecanoyl), Arg$^{34}$, β-Ala$^{35}$)hGLP-1(7-36)NH$_2$

EXAMPLE 116

(Aib$^{8}$, Lys$^{26}$(N$^\epsilon$-decanoyl), Arg$^{34}$, β-Ala$^{35}$)hGLP-1(7-36)NH$_2$

EXAMPLE 117

(Aib$^{8,35}$, Lys$^{34}$(N$^\epsilon$-octanoyl))hGLP-1(7-36)NH$_2$

EXAMPLE 118

(Aib$^{8,35}$, Lys$^{34}$(N$^\epsilon$-tetradecanoyl))hGLP-1(7-36)NH$_2$

EXAMPLE 119

(Aib$^{8,35}$, Lys$^{34}$(N$^\epsilon$-hexadecanoyl))hGLP-1(7-36)NH$_2$

EXAMPLE 120

(Aib$^{8,35}$, Arg$^{26}$, Lys$^{34}$(N$^\epsilon$-octanoyl))hGLP-1(7-36)NH$_2$

EXAMPLE 121

(Aib$^{8,35}$, Arg$^{26}$, Lys$^{34}$(N$^\epsilon$-hexadecanoyl))hGLP-1(7-36)NH$_2$

EXAMPLE 122

(Aib$^{8,35}$, Arg$^{26}$, Lys$^{34}$(N$^\epsilon$-decanoyl))hGLP-1(7-36)NH$_2$

EXAMPLE 123

(Aib$^{8,35}$, Arg$^{25,26}$, Lys$^{34}$(N$^\epsilon$-octanoyl))hGLP-1(7-36)NH$_2$

EXAMPLE 124

(Aib$^{8,35}$, Arg$^{25,26}$, Lys$^{34}$(N$^\epsilon$-tetradecanoyl))hGLP-1(7-36)NH$_2$

EXAMPLE 125

(Aib$^{8,35}$, Arg$^{25,26}$, Lys$^{34}$(N$^\epsilon$-hexadecanoyl))hGLP-1(7-36)NH$_2$

EXAMPLE 126

(Aib$^{8,35}$, Arg$^{25,26}$, Lys$^{34}$(N$^\epsilon$-decanoyl))hGLP-1(7-36)NH$_2$

EXAMPLE 127

(Aib$^{8,35}$, Lys$^{25}$, Arg$^{26}$, Lys$^{34}$(N$^\epsilon$-octanoyl))hGLP-1(7-36)NH$_2$

EXAMPLE 128

(Aib$^{8,35}$, Lys$^{25}$, Arg$^{26}$, Lys$^{34}$(N$^\epsilon$-tetradecanoyl))hGLP-1(7-36)NH$_2$

EXAMPLE 129

(Aib$^{8,35}$, Lys$^{25}$, Arg$^{26}$, Lys$^{34}$(N$^\epsilon$-hexadecanoyl))hGLP-1(7-36)NH$_2$

EXAMPLE 130

(Aib-$^{8,35}$, Lys$^{36}$(N$^\epsilon$-octanoyl))hGLP-1(7-36)NH$_2$

EXAMPLE 131

(Aib$^{8,35}$, Lys$^{36}$(N$^\epsilon$-tetradecanoyl))hGLP-1(7-36)NH$_2$

EXAMPLE 132

(Aib$^{8,35}$, Lys$^{36}$(N$^\epsilon$-hexadecanoyl))hGLP-1(7-36)NH$_2$

EXAMPLE 133

(Aib$^{8,35}$, Arg$^{26}$, Lys$^{36}$(N$^\epsilon$-octanoyl))hGLP-1(7-36)NH$_2$

EXAMPLE 134

(Aib$^{8,35}$, Arg$^{26}$, Lys$^{36}$(N$^\epsilon$-tetradecanoyl))hGLP-1(7-36)NH$_2$

EXAMPLE 135

(Aib$^{8,35}$, Arg$^{26}$, Lys$^{36}$(N$^\epsilon$-hexadecanoyl))hGLP-1(7-36)NH$_2$

EXAMPLE 136

(Aib$^{8,35}$, Arg$^{26,34}$, Lys$^{36}$(N$^\epsilon$-octanoyl))hGLP-1(7-36)NH$_2$

EXAMPLE 137

(Aib$^{8,35}$, Arg$^{26,34}$, Lys$^{36}$(N$^\epsilon$-hexadecanoyl))hGLP-1(7-36)NH$_2$

EXAMPLE 138

(Aib$^{8,35}$, Arg$^{26,34}$, Lys$^{38}$(N$^\epsilon$-octanoyl))hGLP-1(7-38)NH$_2$

EXAMPLE 139

(Aib$^{8,35}$, Arg$^{26,34}$, Lys$^{38}$(N$^\epsilon$-decanoyl))hGLP-1(7-38)NH$_2$

EXAMPLE 140

(Aib$^{8,35}$, Arg$^{26,34}$, Lys$^{38}$(N$^\epsilon$-tetradecanoyl))hGLP-1(7-38)NH$_2$

EXAMPLE 141

(Aib$^{8,35}$, Arg$^{26,34}$, Lys$^{38}$(N$^\epsilon$-hexadecanoyl))hGLP-1(7-38)NH$_2$

EXAMPLE 142

(Aib$^{8,35,37}$, Arg$^{25,26,34}$, Lys$^{38}$(N$^\epsilon$-octanoyl))hGLP-1(7-38)NH$_2$

EXAMPLE 143

(Aib$^{8,35,37}$, Arg$^{25,26,34}$, Lys$^{38}$(N$^\epsilon$-decanoyl))hGLP-1(7-38)NH$_2$

EXAMPLE 144

(Aib$^{8,35,37}$, Arg$^{25,26,34}$, Lys$^{38}$(N$^\epsilon$-tetradecanoyl))hGLP-1(7-38)NH$_2$

EXAMPLE 145

(Aib$^{8,35,37}$, Arg$^{25,26,34}$, Lys$^{38}$(N$^\epsilon$-hexadecanoyl))hGLP-1(7-38)NH$_2$

EXAMPLE 146

(Aib$^{8,35,37}$, Arg$^{26,34}$, Lys$^{38}$(N$^\epsilon$-octanoyl))hGLP 1(7-38)NH$_2$

EXAMPLE 147

(Aib$^{8,35,37}$, Arg$^{26,34}$, Lys$^{38}$(N$^\epsilon$-decanoyl))hGLP-1(7-38)NH$_2$

EXAMPLE 148

(Aib$^{8,35,37}$, Arg$^{26,34}$, Lys$^{38}$(N$^\epsilon$-hexadecanoyl))hGLP-1(7-38)NH$_2$

EXAMPLE 149

(Aib$^{8,35,37}$, Arg$^{25,26,34}$, Lys$^{38}$(N$^\epsilon$-octanoyl))hGLP-1(7-38)NH$_2$

EXAMPLE 150

(Aib$^{8,35,37}$, Arg$^{25,26,34}$, Lys$^{38}$(N$^\epsilon$-decanoyl))hGLP-1(7-38)NH$_2$

EXAMPLE 151

(Aib$^{8,35,37}$, Arg$^{25,26,34}$, Lys$^{38}$(N$^\epsilon$-tetradecanoyl))hGLP-1(7-38)NH$_2$

EXAMPLE 152

(Aib$^{8,35,37}$, Arg$^{25,26,34}$, Lys$^{38}$(N$^\epsilon$-hexadecanoyl))hGLP-1(7-38)NH$_2$

EXAMPLE 153

(Aib$^{8,35}$, Lys$^{25}$, Arg$^{26,34}$, Lys$^{36}$(N$^\epsilon$-octanoyl))hGLP-1(7-36)NH$_2$

EXAMPLE 154

(Aib$^{8,35}$, Lys$^{25}$, Arg$^{26,34}$, Lys$^{36}$(N$^\epsilon$-tetradecanoyl))hGLP-1(7-36)NH$_2$

EXAMPLE 155

(Aib$^{8,35}$, Lys$^{25}$, Arg$^{26,34}$, Lys$^{36}$(N$^\epsilon$-hexadecanoyl))hGLP-1(7-36)NH$_2$

EXAMPLE 156

(Aib$^{8,35}$, Arg$^{25,26,34}$, Lys$^{36}$(N$^\epsilon$-octanoyl))hGLP-1(7-36)NH$_2$

EXAMPLE 157

(Aib$^{8,35}$, Arg$^{25,26,34}$, Lys$^{36}$(N$^\epsilon$-tetradecanoyl))hGLP-1(7-36)NH$_2$

EXAMPLE 158

(Aib$^{8,35}$, Arg$^{25,26,34}$, Lys$^{36}$(N$^\epsilon$-hexadecanoyl))hGLP-1(7-36)NH$_2$

EXAMPLE 159

(Aib$^{8,35}$, Arg$^{25,26,34}$, Lys$_{36}$(N$^\epsilon$-decanoyl))hGLP-1(7-36)NH$_2$

EXAMPLE 160

(Aib$^{3}$, Lys$^{34}$(N$^\epsilon$-octanoyl), β-Ala$^{35}$)hGLP-1(7-36)NH$_2$

EXAMPLE 161

(Aib$^{8}$, Lys$^{34}$(N$^\epsilon$-tetradecanoyl), β-Ala$^{35}$)hGLP-1(7-36)NH$_2$

EXAMPLE 162

(Aib$^{8}$, Lys$^{34}$(N$^\epsilon$-hexadecanoyl), β-Ala$^{35}$)hGLP-1(7-36)NH$_2$

EXAMPLE 163

(Aib$^{8}$, A6c$^{32}$, Lys$^{34}$(N$_\epsilon$-octanoyl), β-Ala$^{35}$)hGLP-1(7-36)NH$_2$

EXAMPLE 164

(Aib$^{8}$, Glu$^{23}$, Lys$^{34}$(N$_\epsilon$-octanoyl), β-Ala$^{35}$)hGLP-1(7-36)NH$_2$

EXAMPLE 165

(Aib$^{8}$, Glu$^{23}$, A6c$^{32}$, Lys$^{34}$(N$_\epsilon$-octanoyl), β-Ala$^{35}$)hGLP-1(7-36)NH

EXAMPLE 166

(Aib$^{8}$, Arg$^{26}$, Lys$^{34}$(N$^\epsilon$-octanoyl), β-Ala$^{35}$)hGLP-1(7-36)NH$_2$

EXAMPLE 167

(Aib$^{8}$, Arg$^{26}$, Lys$^{34}$(N$^\epsilon$-tetradecanoyl), β-Ala$^{35}$)hGLP-1(7-36)NH$_2$

EXAMPLE 168

(Aib$^{8}$, Arg$^{26}$, Lys$^{34}$(N$^\epsilon$-hexadecanoyl), β-Ala$^{35}$)hGLP-1(7-36)NH$_2$

EXAMPLE 169

(Aib$^{8}$, Arg$^{26}$, Lys$^{34}$(N$^\epsilon$-decanoyl), β-Ala$^{35}$)hGLP-1(7-36)NH$_2$

EXAMPLE 170

(Aib$^{8}$, Arg$^{25,26}$, Lys$^{34}$(N$^\epsilon$-octanoyl), β-Ala$^{35}$)hGLP-1(7-36)NH$_2$

EXAMPLE 171

(Aib$^{8}$, Arg$^{25,26}$, Lys$^{34}$(N$^\epsilon$-tetradecanoyl), β-Ala$^{35}$)hGLP-1(7-36)NH$_2$

EXAMPLE 172

(Aib$^{8}$, Arg$^{25,26}$, Lys$^{34}$(N$^\epsilon$-hexadecanoyl), β-Ala$^{35}$)hGLP-1(7-36)NH$_2$

EXAMPLE 173

(Aib$^{8}$, Arg$^{25,26}$, Lys$^{34}$(N$^\epsilon$-decanoyl), β-Ala$^{35}$)hGLP-1(7-36)NH$_2$

EXAMPLE 174

(Aib$^{8}$, Lys$^{25}$, Arg$^{26}$, Lys$^{34}$(N$^\epsilon$-octanoyl), β-Ala$^{35}$)hGLP-1(7-36)NH$_2$

EXAMPLE 175

(Aib$^{8}$, Lys$^{25}$, Arg$^{26}$, Lys$^{34}$(N$^\epsilon$-tetradecanoyl), β-Ala 3)hGLP-1(7-36)NH$_2$

EXAMPLE 176

(Aib$^{8}$, Lys$^{25}$, Arg$^{26}$, Lys$^{34}$(N$^\epsilon$hexadecanoyl), β-Ala$^{35}$)hGLP-1(7-36)NH$_2$

EXAMPLE 177

(Aib$^{8}$, β-Ala$^{35}$, Lys$^{36}$(N$^\epsilon$-octanoyl))hGLP-1(7-36)NH$_2$

EXAMPLE 178

(Aib$^{3}$, β-Ala$^{35}$, Lys$^{36}$(N$^\epsilon$-tetradecanoyl))hGLP-1(7-36)NH$_2$

EXAMPLE 179

(Aib$^{8}$, β-Ala$^{35}$, Lys$^{36}$(N$^\epsilon$-hexadecanoyl))hGLP-1(7-36)NH$_2$

EXAMPLE 180

(Aib$^{8}$, Arg$^{26}$, β-Ala$^{35}$, Lys$^{36}$(N$^\epsilon$-octanoyl))hGLP-1(7-36)NH$_2$

EXAMPLE 181

(Aib$^8$, Arg$^{26}$, β-Ala$^{35}$, Lys$^{36}$(N$^ε$-tetradecanoyl))hGLP-1(7-36)NH$_2$

EXAMPLE 182

(Aib$^8$, Arg$^{26}$, β-Ala$^{36}$, Lys$^{36}$(N$^ε$-hexadecanoyl))hGLP-1(7-36)NH$_2$

EXAMPLE 183

(Aib$^8$, Arg$^{26,34}$, β-Ala$^{35}$, Lys$^{36}$(N$^ε$-octanoyl))hGLP-1(7-36)NH$_2$

EXAMPLE 184

(Aib$^8$, Arg$^{26,34}$, β-Ala$^{35}$, Lys$^{36}$(N$^ε$-tetradecanoyl))hGLP-1(7-36)NH$_2$

EXAMPLE 185

(Aib$^8$, Arg$^{26,34}$, β-Ala$^{35}$, Lys$^{36}$(N$^ε$-hexadecanoyl))hGLP-1(7-36)NH$_2$

EXAMPLE 186

(Aib$^8$, Arg$^{26,34}$, β-Ala$^{35}$, Lys$^{36}$(N$^ε$-decanoyl))hGLP-1(7-36)NH$_2$

EXAMPLE 187

(Aib$^8$, Lys$^{25}$, Arg$^{26,34}$, β-Ala$^{35}$, Lys$^{36}$(N$^ε$-octanoyl))hGLP-1(7-36)NH$_2$

EXAMPLE 188

(Aib$^8$, Lys$^{25}$, Arg$^{26,34}$, Lys$^{36}$(N$^ε$-tetradecanoyl), β-Ala$^{35}$)hGLP-1(7-36)NH$_2$

EXAMPLE 189

(Aib$^8$, Lys$^{25}$, Arg$^{26,34}$, β-Ala$^{35}$, Lys$^{36}$(N$^ε$-hexadecanoyl))hGLP-1(7-36)NH$_2$

EXAMPLE 190

(Aib$^8$, Arg$^{25,26,34}$, β-Ala$^{35}$, Lys$^{36}$(N$^ε$-octanoyl))hGLP-1(7-36)NH$_2$

EXAMPLE 191

(Aib$^8$, Arg$^{25,26,34}$, β-Ala$^{35}$, Lys$^{36}$(N$^ε$-tetradecanoyl))hGLP-1(7-36)NH$_2$

EXAMPLE 192

(Aib$^8$, Arg$^{25,26,34}$, β-Ala$^{35}$, Lys$^{36}$(N$^ε$-hexadecanoyl))hGLP-1(7-36)NH$_2$

EXAMPLE 193

(Aib$^8$, Arg$^{25,26,34}$, β-Ala$^{35}$, Lys$^{36}$(N$^ε$-decanoyl))hGLP-1(7-36)NH$_2$

EXAMPLE 194

(Aib$^{8,35}$, Lys$^{26}$(N$^ε$-octanoyl), A6c$^{32}$, Arg$^{34}$)hGLP-1(7-36)NH$_2$

EXAMPLE 195

(Aib$^{8,35}$, Lys$^{26}$(N$^ε$-tetradecanoyl), A6c$^{32}$, Arg$^{34}$)hGLP-1(7-36)NH$_2$

EXAMPLE 196

(Aib$^{8,35}$, Lys$^{26}$(N$^ε$-hexadecanoyl), A6c$^{32}$, Arg$^{34}$)hGLP-1(7-36)NH$_2$

EXAMPLE 197

(Aib$^{8,35}$, A6c$^{32}$, Lys$^{34}$(N$^ε$-octanoyl))hGLP-1(7-36)NH$_2$

EXAMPLE 198

(Aib$^{8,35}$, A6c$^{32}$, Lys$^{34}$(N$^ε$-tetradecanoyl))hGLP-1(7-36)NH$_2$

EXAMPLE 199

(Aib$^{8,35}$, A6c$^{32}$, Lys$^{34}$(N$^ε$-hexadecanoyl))hGLP-1(7-36)NH$_2$

EXAMPLE 200

(Aib$^{8,35}$, Arg$^{26}$, A6c$^{32}$, Lys$^{34}$(N$^ε$-octanoyl))hGLP-1(7-36)NH$_2$

EXAMPLE 201

(Aib$^{8,35}$, Arg$^{26}$, A6c$^{32}$, Lys$^{34}$(N$^ε$-tetradecanoyl))hGLP-1(7-36)NH$_2$

EXAMPLE 202

(Aib$^{8,35}$, A6c$^{32}$, Lys$^{36}$(N$^ε$-octanoyl))hGLP-1(7-36)NH$_2$

EXAMPLE 203

(Aib$^{8,35}$, A6c$^{32}$, Lys$^{36}$(N$^ε$-tetradecanoyl))hGLP-1(7-36)NH$_2$

EXAMPLE 204

(Aib$^{8,35}$, A6c$^{32}$, Lys$^{36}$(N$^ε$-hexadecanoyl))hGLP-1(7-36)NH$_2$

EXAMPLE 205

(Aib$^{8,35}$, Arg$^{26}$, A6c$^{32}$, Lys$^{36}$(N$^ε$-octanoyl))hGLP-1(7-36)NH$_2$

EXAMPLE 206

(Aib$^{8,35}$, Arg$^{26}$, A6c$^{32}$, Lys$^{36}$(N$^\epsilon$-tetradecanoyl))hGLP-1(7-36)NH$_2$

EXAMPLE 207

(Aib$^{8,35}$, Arg$^{26}$, A6c$^{32}$, Lys$^{36}$(N$^\epsilon$-hexadecanoyl))hGLP-1(7-36)NH$_2$

EXAMPLE 208

(Aib$^{8,35}$, Arg$^{26,34}$, A6c$^{32}$, Lys$^{36}$(N$^\epsilon$-octanoyl))hGLP-1(7-36)NH$_2$

EXAMPLE 209

(Aib$^{8,35}$, Arg$^{26,34}$, A6c$^{32}$, Lys$^{36}$(N$^\epsilon$-decanoyl))hGLP-1(7-36)NH$_2$

EXAMPLE 210

(Aib$^{8,35}$, Arg$^{26,34}$, A6c$^{32}$, Lys$^{36}$(N$^\epsilon$-tetradecanoyl))hGLP-1(7-36)NH$_2$

EXAMPLE 211

(Aib$^{8,35}$, Arg$^{26,34}$, A6c$^{32}$, Lys$^{36}$(N$^\epsilon$-hexadecanoyl))hGLP-1(7-36)NH$_2$

EXAMPLE 212

(Aib$^{8,24,35}$, Lys$^{26}$(N$^\epsilon$-octanoyl), Arg$^{34}$)hGLP-1(7-36)NH$_2$

EXAMPLE 213

(Aib$^{8,24,35}$, Lys$^{26}$(N$^\epsilon$-tetradecanoyl), Arg$^{34}$)hGLP-1(7-36)NH$_2$

EXAMPLE 214

(Aib$^{8,24,35}$, Lys$^{26}$(N$^\epsilon$-hexadecanoyl), Arg$^{34}$)hGLP-1(7-36)NH$_2$

EXAMPLE 215

(Aib$^{8,24,35}$, Arg$^{26}$, Lys$^{34}$(N$^\epsilon$-octanoyl))hGLP-1(7-36)NH$_2$

EXAMPLE 216

(Aib$^{8,24,35}$, Arg$^{26}$, Lys$^{34}$(N$^\epsilon$-tetradecanoyl))hGLP-1(7-36)NH$_2$

EXAMPLE 217

(Aib$^{8,24,35}$, Arg$^{26}$, Lys$^{34}$(N$^\epsilon$-hexadecanoyl))hGLP-1(7-36)NH$_2$

EXAMPLE 218

(Aib$^{8,24,35}$, Arg$^{26,34}$, Lys$^{36}$(N$^\epsilon$-octanoyl))hGLP-1(7-36)NH$_2$

EXAMPLE 219

(Aib$^{8,24,35}$, Arg$^{26,34}$, Lys$^{36}$(N$^\epsilon$-tetradecanoyl))hGLP-1(7-36)NH$_2$

EXAMPLE 220

(Aib$^{8,24,35}$, Arg$^{26,34}$, Lys$^{36}$(N$^\epsilon$-hexadecanoyl))hGLP-1(7-36)NH$_2$

EXAMPLE 221

(Aib$^{8,24,35}$, Glu$^{23}$, A6C$^{32}$, Lys$^{34}$(N$_\epsilon$-octanoyl))hGLP-1(7-36)NH$_2$

EXAMPLE 222

(Aib$^{8,35}$, Glu$^{23}$, Lys$^{26}$(N$^\epsilon$-octanoyl), Arg$^{34}$)hGLP-1(7-36)NH$_2$

EXAMPLE 223

(Aib$^{8,35}$, Glu$^{23}$, Lys$^{26}$(N$^\epsilon$-tetradecanoyl), Arg$^{34}$)hGLP-1(7-36)NH$_2$

EXAMPLE 224

(Aib$^{8,35}$, Glu$^{23}$, Lys$^{26}$(N$^\epsilon$-hexadecanoyl), Arg$^{34}$)hGLP-1(7-36)NH$_2$

EXAMPLE 225

(Aib$^{8,35}$, Glu$^{23}$, Lys$^{34}$(N$_\epsilon$-octanoyl))hGLP-1(7-36)NH$_2$

EXAMPLE 226

(Aib$^{8,35}$, Glu$^{23}$, A6c$^{32}$, Lys$^{34}$(N$_\epsilon$-octanoyl))hGLP-1(7-36)NH$_2$

EXAMPLE 227

(Aib$^{8,35}$, Glu$^{23}$, Arg$^{26}$, Lys$^{34}$(N$^\epsilon$-octanoyl))hGLP-1(7-36)NH$_2$

EXAMPLE 228

(Aib$^{8,35}$, Glu$^{23}$, Arg$^{26}$, Lys$^{34}$(N$^\epsilon$-tetradecanoyl))hGLP-1(7-36)NH$_2$

EXAMPLE 229

(Aib$^{8,35}$, Glu$^{23}$, Arg$^{26}$, Lys$^{34}$(N$^\epsilon$-hexadecanoyl))hGLP-1(7-36)NH$_2$

EXAMPLE 230

(Aib$^{8,35}$, Glu$^{23}$, Lys$^{36}$(N$^\epsilon$-octanoyl))hGLP-1(7-36)NH$_2$

EXAMPLE 231

(Aib$^{8,35}$, Glu$^{23}$, Lys$^{36}$(N$^\epsilon$-tetradecanoyl))hGLP-1(7-36)NH$_2$

EXAMPLE 232

(Aib$^{8,35}$, Glu$^{23}$, Lys$_{36}$(N$^\epsilon$-hexadecanoyl))hGLP-1(7-36)NH$_2$

EXAMPLE 233

(Aib$^{8,35}$, Glu$^{23}$, Arg$^{26,34}$, Lys$^{36}$(N$^\epsilon$-octanoyl))hGLP-1(7-36)NH$_2$

EXAMPLE 234

(Aib$^{8,35}$, Glu$^{23}$, Arg$^{26,34}$, Lys$^{36}$(N$^\epsilon$-tetradecanoyl))hGLP-1(7-36)NH$_2$

EXAMPLE 235

(Aib$^{8,35}$, Glu$^{23}$, Arg$^{26,34}$, Lys$^{36}$(N$^\epsilon$-hexadecanoyl))hGLP-1(7-36)NH$_2$

EXAMPLE 236

(Aib$^{8,30,35}$, Lys$^{26}$(N$^\epsilon$-octanoyl), Arg$^{34}$)hGLP-1(7-36)NH$_2$

EXAMPLE 237

(Aib$^{8,30,35}$, Lys$^{26}$(N$^\epsilon$-tetradecanoyl), Arg$^{34}$)hGLP-1(7-36)NH$_2$

EXAMPLE 238

(Aib$^{8,30,35}$, Lys$^{26}$(N$^\epsilon$-hexadecanoyl), Arg$^{34}$)hGLP-1(7-36)NH$_2$

EXAMPLE 239

(Aib$^{8,30,35}$, Arg$^{26}$, Lys$^{34}$(N$^\epsilon$-octanoyl))hGLP-1(7-36)NH$_2$

EXAMPLE 240

(Aib$^{8,30,35}$, Arg$^{26}$, Lys$^{34}$(N$^\epsilon$-tetradecanoyl))hGLP-1(7-36)NH$_2$

EXAMPLE 241

(Aib$^{8,30,35}$, Arg$^{26}$, Lys$^{34}$(N$^\epsilon$-hexadecanoyl))hGLP-1(7-36)NH$_2$

EXAMPLE 242

(Aib$^{8,30,35}$, Arg$^{26,34}$, Lys$^{36}$(N$^\epsilon$-octanoyl))hGLP-1(7-36)NH$_2$

EXAMPLE 243

(Aib$^{8,30,35}$, Arg$^{26,34}$, Lys$^{36}$(N$^\epsilon$-tetradecanoyl))hGLP-1(7-36)NH$_2$

EXAMPLE 244

(Aib$^{8,30,35}$, Arg$^{26,34}$, Lys$^{36}$(N$^\epsilon$-hexadecanoyl))hGLP-1(7-36)NH$_2$

EXAMPLE 245

(Aib$^{8,35}$, Glu$^{23}$, A6c$^{32}$, Lys$^{36}$(N$^\epsilon$-octanoyl))hGLP-1(7-36)NH$_2$

EXAMPLE 246

(Aib$^{8,35}$, Glu$^{23}$, A6c$^{32}$, Lys$^{36}$(N$^\epsilon$-tetradecanoyl))hGLP 1(7-36)NH$_2$

EXAMPLE 247

(Aib$^{8,35}$, Glu$^{23}$, A6C$^{32}$, Lys$^{36}$(N$^\epsilon$-hexadecanoyl))hGLP-1(7-36)NH$_2$

EXAMPLE 248

(Aib$^{8,35}$, Glu$^{23}$, Arg$^{26,34}$, A6c$^{32}$, Lys$^{36}$(N$^\epsilon$-octanoyl))hGLP-1(7-36)NH$_2$

EXAMPLE 249

(Aib$^{8,35}$, Glu$^{23}$, Arg$^{26,34}$, A6c$^{32}$, Lys$^{36}$(N$^\epsilon$-tetradecanoyl))hGLP-1(7-36)NH$_2$

EXAMPLE 250

(Aib$^{8,35}$, Glu$^{23}$, Arg$^{26,34}$, A6c$^{32}$, Lys$^{36}$(N$^\epsilon$-hexadecanoyl))hGLP-1(7-36)NH$_2$

EXAMPLE 251

(Aib$^{8,24,35}$, Glu$^{23}$, Arg$^{26,34}$, A6c$^{32}$, Lys$^{36}$(N$^\epsilon$-octanoyl))hGLP-1(7-36)NH$_2$

EXAMPLE 252

(Aib$^{8,24,35}$, Glu$^{23}$, Arg$^{26,34}$, A6c$^{32}$, Lys$^{36}$(N$^\epsilon$-tetradecanoyl))hGLP-1(7-36)NH$_2$

EXAMPLE 253

(Aib$^{8,24,35}$, Glu$^{23}$, Arg$^{26,34}$, A6c$^{32}$, Lys$^{36}$(N$^\epsilon$-hexadecanoyl))hGLP-1(7-36)NH$_2$

EXAMPLE 254

(Aib$^{8,24,30,35}$, Glu$^{23}$, Arg$^{26,34}$, A6c$^{32}$, Lys$^{36}$(N$^\epsilon$-octanoyl))hGLP-1(7-36)NH$_2$

EXAMPLE 255

(Aib$^{8,24,30,35}$, Glu$^{23}$, Arg$^{26,34}$, A6c$^{32}$, Lys$^{36}$(N$^\epsilon$-tetradecanoyl))hGLP-1(7-36)NH$_2$

EXAMPLE 256

(Aib$^{8,24,30,35}$, Glu$^{23}$, Arg$^{26,34}$, A6c$^{32}$, Lys$^{36}$(N$^\epsilon$-hexadecanoyl))hGLP-1(7-36)NH$_2$

EXAMPLE 257

(($N^\alpha$-HEPES-His)$^7$, Aib$^{35}$)hGLP-1(7-36)NH$_2$

EXAMPLE 258

(($N^\alpha$-HEPES-His)$^7$, β-Ala$^{35}$)hGLP-1(7-36)NH$_2$

EXAMPLE 259

(($N^\alpha$-HEPES-His)$^7$, Aib$^8$, β-Ala$^{35}$)hGLP-1(7-36)NH$_2$

EXAMPLE 260

(($N^\alpha$-HEPA-His)$^7$, Aib$^{35}$)hGLP-1(7-36)NH$_2$

EXAMPLE 261

(($N^\alpha$-HEPA-His)$^7$, β-Ala$^{35}$)hGLP-1(7-36)NH$_2$

EXAMPLE 262

(($N^\alpha$-HEPA-His)$^7$, Aib$^8$, β-Ala$^{35}$)hGLP-1(7-36)NH$_2$

EXAMPLE 263

(($N^\alpha$-tetradecanoyl-His)$^7$, Aib$^{35}$)hGLP-1(7-36)NH$_2$

EXAMPLE 264

(($N^\alpha$-tetradecanoyl-His)$^7$, β-Ala$^{35}$)hGLP-1(7-36)NH$_2$

EXAMPLE 265

(($N^\alpha$-tetradecanoyl-His)$^7$, Aib$^{8,35}$)hGLP-1(7-36)NH$_2$

EXAMPLE 266

(($N^\alpha$-tetradecanoyl-His)$^7$, Aib$^8$, β-Ala$^{35}$)hGLP-1(7-36)NH$_2$

EXAMPLE 267

(($N^\alpha$-tetradecanoyl-His)$^7$, Arg$^{26,34}$, Aib$^{35}$)hGLP-1(7-36)NH$_2$

EXAMPLE 268

(($N^\alpha$-tetradecanoyl-His)$^7$, Arg$^{26,34}$, β-Ala$^{35}$)hGLP-1(7-36)NH$_2$

EXAMPLE 269

(($N^\alpha$-tetradecanoyl-His)$^7$, Aib$^{8,35}$, Arg$^{26,34}$)hGLP-1(7-36)NH$_2$

EXAMPLE 270

(($N^\alpha$-tetradecanoyl-His)$^7$, Aib$^8$, Arg$^{26,34}$, β-Ala$^{35}$)hGLP-1(7-36)NH$_2$

EXAMPLE 271

(($N^\alpha$-tetradecanoyl-His)$^7$, Arg$^{25,26,34}$, β-Ala$^{35}$)hGLP-1(7-36)NH$_2$

EXAMPLE 272

(($N^\alpha$-tetradecanoyl-His)$^7$, Aib$^{8,35}$, Arg$^{25,26,34}$)hGLP-1(7-36)NH$_2$

EXAMPLE 273

(($N^\alpha$-tetradecanoyl-His)$^7$, Aib$^8$, Arg$^{25,26,34}$, β-Ala$^{35}$)hGLP-1(7-36)NH$_2$

EXAMPLE 274

(Aib$^{8,35}$, Lys$^{26}$($N^\epsilon$-octanesulfonyl), Arg$^{34}$)hGLP-1(7-36)NH$_2$

EXAMPLE 275

(Aib$^{8,35}$, Lys$^{26}$($N^\epsilon$-dodecanesulfonyl), Arg$^{34}$)hGLP-1(7-36)NH$_2$

EXAMPLE 276

(Aib$^{8,35}$, Lys$^{26}$($N^\epsilon$-hexadecanesulfonyl), Arg$^{34}$)hGLP-1(7-36)NH$_2$

EXAMPLE 277

(Aib$^{8,35}$, Arg$^{26}$, Lys$^{34}$($N^\epsilon$-octanesulfonyl))hGLP-1(7-36)NH$_2$

EXAMPLE 278

(Aib$^{8,35}$, Arg$^{26}$, Lys$^{34}$($N^\epsilon$-dodecanesulfonyl))hGLP-1(7-36)NH$_2$

EXAMPLE 279

(Aib$^{8,35}$, Arg$^{26}$, Lys$^{34}$($N^\epsilon$-hexadecanesulfonyl))hGLP-1(7-36)NH$_2$

EXAMPLE 280

(Aib$^{8,35}$, Arg$^{26,34}$, Lys$^{38}$($N^\epsilon$-octanesulfonyl))hGLP-1(7-36)NH$_2$

EXAMPLE 281

(Aib$^{8,35}$, Arg$^{26,34}$, Lys$^{36}$($N^\epsilon$-hexadecanesulfonyl))hGLP-1(7-36)NH$_2$

EXAMPLE 282

(Aib$^{8,35}$, Asp$^{26}$(1-(4-decylpiperazine)), Arg$^{34}$)hGLP-1(7-36)NH$_2$

EXAMPLE 283

(Aib$^{8,35}$, Asp$^{26}$(1-(4-dodecylpiperazine)), Arg$^{34}$)hGLP-1(7-36)NH$_2$

EXAMPLE 284

(Aib$^{8,35}$, Asp$^{26}$(1-(4-tetradecylpiperazine)), Arg$^{34}$)hGLP-1(7-36)NH$_2$

EXAMPLE 285

(Aib$^{8,35}$, Asp$^{26}$(1-(4-hexadecylpiperazine)), Arg$^{34}$)hGLP-1(7-36)NH$_2$

EXAMPLE 286

(Aib$^{8,35}$, Arg$^{26}$, Asp$^{34}$(1-(4-decylpiperazine)))hGLP-1(7-36)NH$_2$

EXAMPLE 287

(Aib$^{8,35}$, Arg$^{26}$, Asp$^{34}$(1-(4-dodecylpiperazine)))hGLP-1(7-36)NH$_2$

EXAMPLE 288

(Aib$^{8,35}$, Arg$^{26}$, Asp$^{34}$(1-(4-tetradecylpiperazine)))hGLP-1(7-36)NH$_2$

EXAMPLE 289

(Aib$^{8,35}$, Arg$^{26}$, Asp$^{34}$(1-(4-hexadecylpiperazine)))hGLP-1(7-36)NH$_2$

EXAMPLE 290

(Aib$^{8,35}$, Arg$^{26,34}$, Asp$^{36}$(1-(4-decylpiperazine)))hGLP-1(7-36)NH$_2$

EXAMPLE 291

(Aib$^{8,35}$, Arg$^{26,34}$, Asp$^{36}$(1-(4dodecylpiperazine)))hGLP-1(7-36)NH$_2$

EXAMPLE 292

(Aib$^{8,35}$, Arg$^{26,34}$, Asp$^{38}$(1-(4-hexadecylpiperazine)))hGLP-1(7-36)NH$_2$

EXAMPLE 293

(Aib$^{8,35}$, Arg$^{26,34}$, Asp$^{38}$(1-(4-decylpiperazine)))hGLP-1(7-38)NH$_2$

EXAMPLE 294

(Aib$^{8,35}$, Arg$^{26,34}$, Asp$^{38}$(1-(4-dodecylpiperazine)))hGLP-1(7-38)NH$_2$

EXAMPLE 295

(Aib$^{8,35}$, Arg$^{26,34}$, Asp$^{38}$(1-(4-tetradecylpiperazine)))hGLP-1(7-38)NH$_2$

EXAMPLE 296

(Aib$^{8,35}$, Arg$^{26,34}$, Asp$^{38}$(1-(4-hexadecylpiperazine)))hGLP-1(7-38)NH$_2$

EXAMPLE 297

(Aib$^{8,35,37}$, Arg$^{26,34}$, Asp$^{38}$(1-(4-decylpiperazine)))hGLP-1(7-38)NH$_2$

EXAMPLE 298

(Aib$^{8,35,37}$, Arg$^{26,34}$, Asp$^{38}$(1-(4-dodecylpiperazine)))hGLP-1(7-38)NH$_2$

EXAMPLE 299

(Aib$^{8,35,37}$, Arg$^{26,34}$, Asp$^{38}$(1-(4-tetradecylpiperazine)))hGLP-1(7-38)NH$_2$

EXAMPLE 300

(Aib$^{8,35,37}$, Arg$^{26,34}$, Asp$^{38}$(1-(4-hexadecylpiperazine)))hGLP-1(7-38)NH$_2$

EXAMPLE 301

(Aib$^{8,35}$, Arg$^{25,34}$, Asp$^{26}$(1-(4-decylpiperazine)))hGLP-1(7-36)NH$_2$

EXAMPLE 302

(Aib$^{8,35}$, Arg$^{25,34}$, Asp$^{26}$(1-(4-dodecylpiperazine)))hGLP-1(7-36)NH$_2$

EXAMPLE 303

(Aib$^{8,35}$, Arg$^{25,34}$, Asp$^{26}$(1-(4-tetradecylpiperazine)))hGLP-1(7-36)NH$_2$

EXAMPLE 304

(Aib$^{8,35}$, Arg$^{25,34}$, Asp$^{26}$(1-(4-hexadecylpiperazine)))hGLP-1(7-36)NH$_2$

EXAMPLE 305

(Aib$^{8,35}$, Arg$^{25,26}$, Asp$^{34}$(1-(4-decylpiperazine)))hGLP-1(7-36)NH$_2$

EXAMPLE 306

(Aib$^{8,35}$, Arg$^{25,26}$, Asp$^{34}$(1-(4-dodecylpiperazine)))hGLP-1(7-36)NH$_2$

EXAMPLE 307

(Aib$^{8,35}$, Arg$^{25,26}$, Asp$^{34}$(1-(4-tetradecylpiperazine)))hGLP-1(7-36)NH$_2$

EXAMPLE 308

(Aib$^{8,35}$, Arg$^{25,26}$, Asp$^{34}$(1-(4-hexadecylpiperazine)))hGLP-1(7-36)NH$_2$

EXAMPLE 309

(Aib$^{8,35}$, Arg$^{25,26,34}$, Asp$^{36}$(1-(4-decylpiperazine)))hGLP-1(7-36)NH$_2$

EXAMPLE 310

(Aib$^{8,35}$, Arg$^{25,26,34}$, Asp$^{36}$(1-(4-dodecylpiperazine)))hGLP-1(7-36)NH$_2$

EXAMPLE 311

(Aib$^{8,35}$, Arg$^{25,26,34}$, Asp$^{36}$(1-(4-tetradecylpiperazine)))hGLP-1(7-36)NH$_2$

EXAMPLE 312

(Aib$^{8,35}$, Arg$^{25,26,34}$, Asp$^{36}$(1-(4-hexadecylpiperazine)))hGLP-1(7-36)NH$_2$

EXAMPLE 313

(Aib$^{8,35}$, Arg$^{25,26,34}$, Asp$^{38}$(1-(4-decylpiperazine)))hGLP-1(7-38)NH$_2$

EXAMPLE 314

(Aib$^{8,35}$, Arg$^{25,26,34}$, Asp$^{38}$(1-(4-dodecylpiperazine)))hGLP-1(7-38)NH$_2$

EXAMPLE 315

(Aib$^{8,35}$, Arg$^{25,26,34}$, Asp$^{38}$(1-(4-tetradecylpiperazine)))hGLP-1(7-38)NH$_2$

EXAMPLE 316

(Aib$^{8,35}$, Arg$^{25,26,34}$, Asp$^{38}$(1-(4-hexadecylpiperazine)))hGLP-1(7-38)NH$_2$

EXAMPLE 317

(Aib$^{8,35,37}$, Arg$^{25,26,34}$, Asp$^{38}$(1-(4-decylpiperazine)))hGLP-1(7-38)NH$_2$

EXAMPLE 318

(Aib$^{8,35,37}$, Arg$^{25,26,34}$, Asp$^{38}$(1-(4-dodecylpiperazine)))hGLP-1(7-38)NH$_2$

EXAMPLE 319

(Aib$^{8,35,37}$, Arg$^{25,26,34}$, Asp$^{38}$(1-(4-tetradecylpiperazine)))hGLP-1(7-38)NH$_2$

EXAMPLE 320

(Aib$^{8,35,37}$, Arg$^{25,26,34}$, Asp$^{38}$(1-(4-hexadecylpiperazine)))hGLP-1(7-38)NH$_2$

EXAMPLE 321

(Aib$^{8,35}$, Arg$^{26,34}$, Glu$^{36}$(1-dodecylamino))hGLP-1(7-36)NH$_2$

EXAMPLE 322

(Aib$^{8,35}$, Glu$^{26}$(1-dodecylamino), Arg$^{34}$)hGLP-1(7-36)NH$_2$

EXAMPLE 323

(Aib$^{8,35}$, Arg$^{26}$, Glu$^{34}$(1-dodecylamino))hGLP-1(7-36)NH$_2$

EXAMPLE 324

(Aib$^{8,35,37}$, Arg$^{26,34}$, Glu$^{38}$(1-dodecylamino))hGLP-1(7-38)NH$_2$

EXAMPLE 325

(Aib$^{8,35}$, Arg$^{34}$, Lys$^{26}$(N$^{\epsilon}$-(2-(4-decyl-1-piperazine)-acetyl)))hGLP-1(7-36)NH$_2$

EXAMPLE 326

(Aib$^{8,35}$, Arg$^{34}$, Lys$^{26}$(N$^{\epsilon}$-(2-(4-dodecyl-1-piperazine)-acetyl)))hGLP-1(7-36)NH$_2$

EXAMPLE 327

(Aib$^{8,35}$, Arg$^{34}$, Lys$^{26}$(N$^{\epsilon}$-(2-(4-tetradecyl-1-piperazine)-acetyl)))hGLP-1(7-36)NH$_2$

EXAMPLE 328

(Aib$^{8,35}$, Arg$^{34}$, Lys$^{26}$(N$^{\epsilon}$-(2-(4-hexadecyl-1-piperazine)-acetyl)))hGLP-1(7-36)NH$_2$

EXAMPLE 329

(Aib$^{8,35}$, Arg$^{26}$, Lys$^{34}$(N$^{\epsilon}$-(2-(4-decyl-1-piperazine)-acetyl)))hGLP-1(7-36)NH$_2$

EXAMPLE 330

(Aib$^{8,35}$, Arg$^{26}$, Lys$^{34}$(N$^{\epsilon}$-(2-(4-dodecyl-1-piperazine)-acetyl))hGLP-1(7-36)NH$_2$

EXAMPLE 331

(Aib$^{8,35}$, Arg$^{26}$, Lys$^{34}$(N$^{\epsilon}$-(2-(4-tetradecyl-1-piperazine)-acetyl)))hGLP-1(7-36)NH$_2$

EXAMPLE 332

(Aib$^{8,35}$, Arg$^{26}$, Lys$^{34}$(N$^\epsilon$-(2-(4-hexadecyl-1-piperazine)-acetyl)))hGLP-1(7-36)NH$_2$

EXAMPLE 333

(Aib$^{8,35}$, Arg$^{26,34}$, Lys$^{36}$(N$^\epsilon$-(2-(4-decyl-1-piperazine)-acetyl)))hGLP-1(7-36)NH$_2$

EXAMPLE 334

(Aib$^{8,35}$, Arg$^{26,34}$, Lys$^{36}$(N$^\epsilon$-(2-(4-dodecyl-1-piperazine)-acetyl)))hGLP-1(7-36)NH$_2$

EXAMPLE 335

(Aib$^{8,35}$, Arg$^{26,34}$, Lys$^{36}$(N$^\epsilon$-(2-(4-hexadecyl-1-piperazine)-acetyl)))hGLP-1(7-36)NH$_2$

EXAMPLE 336

(Aib$^{8,35}$, Arg$^{26,34}$, Lys$^{38}$(N$^\epsilon$-(2-(4-decyl-1-piperazine)-acetyl)))hGLP-1(7-38)NH$_2$

EXAMPLE 337

(Aib$^{8,35}$, Arg$^{26,34}$, Lys$^{38}$(N$^\epsilon$-(2-(4-dodecyl-1-piperazine)-acetyl)))hGLP-1(7-38)NH$_2$

EXAMPLE 338

(Aib$^{8,35}$, Arg$^{26,34}$, Lys$^{38}$(N$^\epsilon$-(2-(4-tetradecyl-1-piperazine)-acetyl)))hGLP-1(7-38)NH$_2$

EXAMPLE 339

(Aib$^{8,35}$, Arg$^{26,34}$, Lys$^{38}$(N$^\epsilon$-(2-(4-hexadecyl-1-piperazine)-acetyl)))hGLP-1(7-38)NH$_2$

EXAMPLE 340

(Aib$^{8,35,37}$, Arg$^{26,34}$, Lys$^{38}$(N$^\epsilon$-(2-(4-decyl-1-piperazine)-acetyl)))hGLP-1(7-38)NH$_2$

EXAMPLE 341

(Aib$^{8,35,37}$, Arg$^{26,34}$, Lys$^{38}$(N$^\epsilon$-(2-(4-dodecyl-1-piperazine)-acetyl)))hGLP-1(7-38)NH$_2$

EXAMPLE 342

(Aib$^{8,35,37}$, Arg$^{26,34}$, Lys$^{38}$(N$^\epsilon$-(2-(4-tetradecyl-1-piperazine)-acetyl)))hGLP-1(7-38)NH$_2$

EXAMPLE 343

(Aib$^{8,35,37}$, Arg$^{26,34}$, Lys$^{38}$(N$^\epsilon$-(2-(4-hexadecyl-1-piperazine)-acetyl)))hGLP-1(7-38)NH$_2$

EXAMPLE 344

(Aib$^{8,35}$, Arg$^{25,34}$, Lys$^{26}$(N$^\epsilon$-(2-(4-decyl-1-piperazine)-acetyl)))hGLP-1(7-36)NH$_2$

EXAMPLE 345

(Aib$^{8,35}$, Arg$^{25,34}$, Lys$^{26}$(N$^\epsilon$-(2-(4-dodecyl-1-piperazine)-acetyl)))hGLP-1(7-36)NH$_2$

EXAMPLE 346

(Aib$^{8,35}$, Arg$^{25,34}$, Lys$^{26}$(N$^\epsilon$-(2-(4-tetradecyl-1-piperazine)-acetyl)))hGLP-1(7-36)NH$_2$

EXAMPLE 347

(Aib$^{8,35}$, Arg$^{25,34}$, Lys$^{26}$(N$^\epsilon$-(2-(4-hexadecyl-1-piperazine)-acetyl)))hGLP-1(7-36)NH$_2$

EXAMPLE 348

(Aib$^{8,35}$, Arg$^{25,26}$, Lys$^{34}$(N$^\epsilon$-(2-(4-decyl-1-piperazine)-acetyl)))hGLP-1(7-36)NH$_2$

EXAMPLE 349

(Aib$^{8,35}$, Arg$^{25,26}$, Lys$^{34}$(N$^\epsilon$-(2-(4-dodecyl-1-piperazine)-acetyl)))hGLP-1(7-36)NH$_2$

EXAMPLE 350

(Aib$^{8,35}$, Arg$^{25,26}$, Lys$^{34}$(N$^\epsilon$-(2-(4-tetradecyl-1-piperazine)-acetyl)))hGLP-1(7-36)NH$_2$

EXAMPLE 351

(Aib$^{8,35}$, Arg$^{25,26}$, Lys$^{34}$(N$^\epsilon$-(2-(4-hexadecyl-1-piperazine)-acetyl)))hGLP-1(7-36)NH$_2$

EXAMPLE 352

(Aib$^{8,35}$, Arg$^{25,26,34}$, Lys$^{36}$(N$^\epsilon$-(2-(4-decyl-1-piperazine)-acetyl)))hGLP-1(7-36)NH$_2$

EXAMPLE 353

(Aib$^{8,35}$, Arg$^{25,26,34}$, Lys$^{36}$(N$^\epsilon$-(2-(4-dodecyl-1-piperazine)-acetyl)))hGLP-1(7-36)NH$_2$

EXAMPLE 354

(Aib$^{8,35}$, Arg$^{25,26,34}$, Lys$^{36}$(N$^\epsilon$-(2-(4-tetradecyl-1-piperazine)-acetyl)))hGLP-1(7-36)NH$_2$

EXAMPLE 355

(Aib$^{8,35}$, Arg$^{25,26,34}$, Lys$^{36}$(N$^\epsilon$-(2-(4-hexadecyl-1-piperazine)-acetyl)))hGLP-1(7-36)NH$_2$

EXAMPLE 356

(Aib$^{8,35}$, Arg$^{25,26,34}$, Lys$^{38}$(N$^\epsilon$-(2-(4-decyl-1-piperazine)-acetyl)))hGLP-1(7-38)NH$_2$

EXAMPLE 357

(Aib$^{8,35}$, Arg$^{25,26,34}$, Lys$^{38}$(N$^\epsilon$-(2-(4-dodecyl-1-piperazine)-acetyl)))hGLP-1(7-38)NH$_2$

EXAMPLE 358

(Aib$^{8,35}$, Arg$^{25,26,34}$, Lys$^{38}$(N$^\epsilon$-(2-(4-tetradecyl-1-piperazine)-acetyl)))hGLP-1(7-38)NH$_2$

EXAMPLE 359

(Aib$^{8,35}$, Arg$^{25,26,34}$, Lys$^{38}$(N$^\epsilon$-(2-(4-hexadecyl-1-piperazine)-acetyl)))hGLP-1(7-38)NH$_2$

EXAMPLE 360

(Aib$^{8,35,37}$, Arg$^{25,26,34}$, Lys$^{38}$(N$^\epsilon$-(2-(4-decyl-1-piperazine)-acetyl)))hGLP-1(7-38)NH$_2$

EXAMPLE 361

(Aib$^{8,35,37}$, Arg$^{25,26,34}$, Lys$^{38}$(N$^\epsilon$-(2-(4-dodecyl-1-piperazine)-acetyl)))hGLP-1(7-38)NH$_2$

EXAMPLE 362

(Aib$^{8,35,37}$, Arg$^{25,26,34}$, Lys$^{38}$(N$^\epsilon$-(2-(4-tetradecyl-1-piperazine)-acetyl)))hGLP-1(7-38)NH$_2$

EXAMPLE 363

(Aib$^{8,35,37}$, Arg$^{25,26,34}$, Lys$^{38}$(N$^\epsilon$-(2-(4-hexadecyl-1-piperazine)-acetyl))hGLP-1(7-38)NH$_2$

EXAMPLE 364

(Aib$^{8,35}$, Arg$^{26,34}$, Lys$^{36}$(N$^\epsilon$-decanoyl))hGLP-1(7-36)OH

EXAMPLE 365

(Aib$^{8,35}$, Lys$^{25}$, Arg$^{26,34}$, Lys$^{36}$(N$^\epsilon$-decanoyl))hGLP-1(7-36)OH

EXAMPLE 370

(Aib$^{8,35}$, Arg$^{26,34}$, Ava$^{37}$, Ado$^{38}$)hGLP-1(7-38)NH$_2$

EXAMPLE 371

(Aib$^{8,35}$, Arg$^{26,34}$, Asp$^{37}$, Ava$^{38}$, Ado$^{39}$)hGLP-1(7-39)NH$_2$

EXAMPLE 372

(Aib$^{8,35}$, Arg$^{26,34}$, Aun$^{37}$)hGLP-1(7-37)NH$_2$

EXAMPLE 373

(Aib$^{8,17,35}$)hGLP-1(7-36)NH$_2$

EXAMPLE 374

(Aib$^8$, Arg$^{26,34}$, β-Ala$^{35}$, D-Asp$^{37}$, Ava$^{38}$, Aun$^{39}$)hGLP-1(7-39)NH$_2$

EXAMPLE 375

(Gly$^8$, β-Ala$^{35}$)hGLP-1(7-36)NH$_2$

EXAMPLE 376

(Ser$^8$, β-Ala$^{35}$)hGLP-1(7-36)NH$_2$

EXAMPLE 377

(Aib$^8$, Glu$^{22,23}$, β-Ala$^{35}$)hGLP-1(7-36)NH$_2$

EXAMPLE 378

(Gly$^8$, Aib$^{35}$)hGLP-1(7-36)NH$_2$

EXAMPLE 379

(Aib$^8$, Lys$^{18}$, β-Ala$^{35}$)hGLP-1(7-36)NH$_2$

EXAMPLE 380

(Aib$^8$, Leu$^{27}$, β-Ala$^{35}$)hGLP-1(7-36)NH$_2$

EXAMPLE 381

(Aib$^8$, Lys$^{33}$, β-Ala$^{35}$)hGLP-1(7-36)NH$_2$

EXAMPLE 382

(Aib$^8$, Lys$^{18}$, Leu$^{27}$, β-Ala$^{35}$)hGLP-1(7-36)NH$_2$

EXAMPLE 383

(Aib$^8$, D-Arg$^{36}$)hGLP-1(7-36)NH$_2$

EXAMPLE 384

(Aib$^8$, β-Ala$^{35}$, D-Arg$^{37}$)hGLP-1(7-37)NH$_2$

EXAMPLE 385

(Aib$^{8,27}$, β-Ala$^{35}$)hGLP-1(7-36)NH$_2$

EXAMPLE 386

(Aib$^{8,27}$, β-Ala$^{35,37}$, Arg$^{38}$)hGLP-1(7-38)NH$_2$

EXAMPLE 387

(Aib$^{8,27}$, β-Ala$^{35,37}$, Arg$^{38,39}$)hGLP-1(7-39)NH$_2$

EXAMPLE 388

(Aib$^8$, Lys$^{18,27}$, β-Ala$^{35}$)hGLP-1(7-36)NH$_2$

EXAMPLE 389

(Aib$^8$, Lys$^{27}$, β-Ala$^{35}$)hGLP-1(7-36)NH$_2$

EXAMPLE 390

(Aib$^8$, β-Ala$^{35}$, Arg$^{38}$)hGLP-1(7-38)NH$_2$

EXAMPLE 391

(Aib$^8$, Arg$^{26,34}$, β-Ala$^{35}$,)hGLP-1(7-36)NH$_2$

EXAMPLE 392

(Aib$^8$, D-Arg$^{35}$)hGLP-1(7-36)NH$_2$

EXAMPLE 393

(Aib$^8$, β-Ala$^{35}$, Arg$^{37}$)hGLP-1(7-37)NH$_2$

EXAMPLE 394

(Aib$^8$, Phe$^{31}$, β-Ala$^{35}$)hGLP-1(7-36)NH$_2$

EXAMPLE 395

(Aib$^{8,35}$, Phe$^{31}$)hGLP-1(7-36)NH$_2$

EXAMPLE 396

(Aib$^{8,35}$, Nal$^{31}$)hGLP-1(7-36)NH$_2$

EXAMPLE 397

(Aib$^{8,35}$, Nal$^{28,31}$)hGLP-1(7-36)NH$_2$

EXAMPLE 398

(Aib$^{8,35}$, Arg$^{26,34}$, Nal$^{31}$)hGLP-1(7-36)NH$_2$

EXAMPLE 399

(Aib$^{8,35}$, Arg$^{26,34}$, Phe$^{31}$)hGLP-1(7-36)NH$_2$

EXAMPLE 400

(Aib$^{8,35}$, Nal$^{19,31}$)hGLP-1(7-36)NH$_2$

EXAMPLE 401

(Aib$^{8,35}$, Nal$^{12,31}$)hGLP-1(7-36)NH$_2$

EXAMPLE 402

(Aib$^{8,35}$, Lys$^{36}$(N$^\epsilon$-decanoyl))hGLP-1(7-36) NH$_2$

EXAMPLE 403

(Aib$^{8,35}$, Arg$^{34}$, Lys$^{26}$(N$^\epsilon$-decanoyl))hGLP-1(7-36)NH$_2$

EXAMPLE 404

(Aib$^{8,35}$, Arg$^{26,34}$ Lys$^{36}$(N$^\epsilon$-dodecanoyl))hGLP-1(7-36)NH$_2$

EXAMPLE 405

(Aib$^8$, B-Ala$^{35}$, Ser$^{37}$(O-decanoyl))hGLP1(7-37)-NH$_2$

EXAMPLE 406

(Aib$^{8,27}$, β-Ala$^{35,37}$, Arg$^{38}$, Lys$^{39}$(N$^\epsilon$-octanoyl))hGLP-1(7-39)NH$_2$

EXAMPLE 407

(Aib$^8$, Arg$^{26,34}$, β-Ala$^{35}$, Lys$^{37}$(N$^\epsilon$-octanoyl))hGLP-1(7-37)NH$_2$

EXAMPLE 408

(Aib$^8$, Arg$^{26,34}$, β-Ala$^{35}$, Lys$^{37}$(N$^\epsilon$-decanoyl))hGLP-1(7-37)NH$_2$

EXAMPLE 409

(Aib$^8$, Arg$^{26,34}$, β-Ala$^{35}$, Lys$^{37}$(N$^\epsilon$-tetradecanoyl))hGLP-1(7-37)NH$_2$

EXAMPLE 410

(Aib$^8$, Arg$^{26,34}$, β-Ala$^{35}$, Lys$^{37}$(N$^\epsilon$-dodecanoyl))hGLP-1(7-37)NH$_2$

EXAMPLE 411

(Aib$^8$, Arg$^{26,34}$, β-Ala$^{35}$, Lys$^{37}$(N$^\epsilon$-dodecanoyl))hGLP-1(8-37)NH$_2$ Physical data for a representative sampling of the compounds exemplified herein are given in Table 1.

TABLE 1

| Example Number | Mol. Wt. Expected | Mol. Wt. MS(ES) | Purity (HPLC) |
|---|---|---|---|
| 24 | 3351.8 | 3352.2 | 88% |
| 26 | 3340.17 | 3340.9 | 99% |
| 27 | 3353.81 | 3353.9 | 99% |
| 29 | 3353.81 | 3353.9 | 99% |
| 45 | 3352.6 | 3352.5 | 97% |
| 51 | 3326.74 | 3326.6 | 99% |
| 78 | 3395.81 | 3395.5 | 96% |
| 136 | 3494 | 3494 | 99% |
| 364 | 3523.02 | 3523.6 | 99% |
| 365 | 3580.13 | 3580.3 | 95% |
| 369 | 3677.25 | 3677 | 97% |
| 370 | 3692.28 | 3692.4 | 98% |
| 371 | 3807.37 | 3807.3 | 98% |
| 372 | 3579.11 | 3579.7 | 97.90% |
| 373 | 3337.81 | 3338.5 | 94% |
| 374 | 3779.3 | 3779.5 | 94% |
| 375 | 3297.7 | 3297.5 | 99% |

TABLE 1-continued

| Example Number | Mol. Wt. Expected | Mol. Wt. MS(ES) | Purity (HPLC) |
|---|---|---|---|
| 376 | 3327.7 | 3327.4 | 98% |
| 377 | 3398.8 | 3398.7 | 97.50% |
| 378 | 3311.6 | 3311 | 93% |
| 379 | 3366.85 | 3366.5 | 97% |
| 380 | 3309.8 | 3309.4 | 99% |
| 381 | 3354.8 | 3354.5 | 97.70% |
| 382 | 3350.9 | 3350.3 | 97.20% |
| 383 | 3311.73 | 3310.7 | 92% |
| 384 | 3481.95 | 3481.3 | 94.30% |
| 385 | 3281.76 | 3281.6 | 98% |
| 386 | 3509.02 | 3509.1 | 99.40% |
| 387 | 3665.2 | 3665.1 | 99% |
| 388 | 3365.91 | 3365 | 97% |
| 389 | 3324.79 | 3324.2 | 95% |
| 390 | 3539 | 3539.2 | 93% |
| 391 | 3381.74 | 3381.3 | 97% |
| 392 | 3410.89 | 3409.8 | 99% |
| 393 | 3481.95 | 3481.1 | 90% |
| 394 | 3286.76 | 3286.2 | 99.20% |
| 395 | 3300.76 | 3299.4 | 93% |
| 396 | 3350.81 | 3349.4 | 99% |
| 397 | 3400.87 | 3400.1 | 99% |
| 398 | 3406.84 | 3406.4 | 99% |
| 399 | 3356.77 | 3356.6 | 99% |
| 400 | 3384.87 | 3384.43 | 94% |

TABLE 1-continued

| Example Number | Mol. Wt. Expected | Mol. Wt. MS(ES) | Purity (HPLC) |
|---|---|---|---|
| 401 | 3400.87 | 3401.3 | 99% |
| 402 | 3466.03 | 3466.9 | 97.40% |
| 403 | 3522.05 | 3522.06 | 93% |
| 404 | 3550.11 | 3550.2 | 98% |
| 405 | 3567.09 | | 99% |
| 406 | 3763.38 | 3763.2 | 95% |
| 407 | 3636.15 | 3635.8 | 99% |
| 408 | 3664.21 | 3663.3 | 99% |
| 409 | 3720.32 | 3719.5 | 99% |
| 410 | 3692.27 | 3691.7 | 99% |
| 411 | 3555.13 | 3554.4 | 99% |

What is claimed is:

1. A method for treating a disease selected from the group consisting of Type I diabetes and Type II diabetes in a subject in need thereof, said method comprising administering to said subject an effective amount of a compound according to the formula [Aib$^{8,35}$]hGLP-1(7-36)NH$_2$(SEQ ID NO:2), or a pharmaceutically acceptable salt thereof.

* * * * *